(12) United States Patent
Vadlamani et al.

(10) Patent No.: US 10,077,422 B2
(45) Date of Patent: Sep. 18, 2018

(54) MICROALGAE HARVESTING USING STIMULI-SENSITIVE HYDROGELS

(71) Applicant: The University of Toledo, Toledo, OH (US)

(72) Inventors: Agasteswar Vadlamani, Toledo, OH (US); Xiaofei Zhao, Toledo, OH (US); Sridhar Viamajala, Sylvania, OH (US); Sasidhar Varanasi, Toledo, OH (US)

(73) Assignee: The University of Toledo, Toledo, OH (US)

( * ) Notice: Subject to any disclaimer, the term of this patent is extended or adjusted under 35 U.S.C. 154(b) by 71 days.

(21) Appl. No.: 15/263,625

(22) Filed: Sep. 13, 2016

(65) Prior Publication Data

US 2017/0088811 A1    Mar. 30, 2017

Related U.S. Application Data

(60) Provisional application No. 62/233,782, filed on Sep. 28, 2015.

(51) Int. Cl.
 *C12M 1/00* (2006.01)
 *C12M 3/00* (2006.01)
 *C12N 1/02* (2006.01)

(52) U.S. Cl.
 CPC ............. *C12M 47/02* (2013.01); *C12N 1/02* (2013.01)

(58) Field of Classification Search
 CPC ...... C12M 47/00; C12M 47/02; C12M 47/04; C12M 47/10; C12M 47/12
 See application file for complete search history.

(56) References Cited

U.S. PATENT DOCUMENTS

| | | | | |
|---|---|---|---|---|
| 5,820,767 A | * | 10/1998 | Kane | B01D 29/05 210/787 |
| 9,714,945 B2 | * | 7/2017 | Miltenyi | G01N 33/58 |
| 2007/0101463 A1 | * | 5/2007 | Gupta | A01H 4/001 800/319 |
| 2008/0248552 A1 | * | 10/2008 | Castillo Fernandez | B01F 7/1635 435/243 |
| 2011/0263021 A1 | * | 10/2011 | Stobbe | C12M 23/34 435/398 |
| 2017/0073625 A1 | * | 3/2017 | Kasuto | C12M 23/34 |

* cited by examiner

*Primary Examiner* — Nathan A Bowers
(74) *Attorney, Agent, or Firm* — MacMillan, Sobanski & Todd, LLC

(57) ABSTRACT

A harvesting device and methods of harvesting (i.e., dewatering) algae are described. The harvesting device and methods involve the use of stimuli-sensitive hydrogels.

16 Claims, 15 Drawing Sheets
(7 of 15 Drawing Sheet(s) Filed in Color)

MICROALGAE HARVESTING USING STIMULI-SENSITIVE HYDROGELS

RELATED APPLICATIONS

This application claims priority to U.S. Provisional Application Ser. No. 62/223,782 filed under 35 U.S.C. § 111(b) on Sep. 28, 2015, the disclosure of which is incorporated herein by reference in its entirety.

STATEMENT REGARDING FEDERALLY SPONSORED RESEARCH

This invention was made with government support under grant number CHE-1230609 awarded by the National Science Foundation, and grant number DE-EE0005993 awarded by the United States Department of Energy. The government has certain rights in this invention.

BACKGROUND OF THE INVENTION

Biofuels produced from microalgae, at an estimated oil content of 40%, promise 10 to 100 times greater yield per land acre than other crops. Currently, a major hurdle for commercial-scale production of fuels from microalgae is recovering algal biomass from growth media with minimal cost and energy input. When cultivated in open raceway ponds, microalgae concentrations are very low—typically 0.1% (w/w). For fuel production, the challenge is therefore to harvest these dilute cultures efficiently and economically. Also, commercial-scale harvesting methods should also allow for recycling of water and unutilized water-soluble nutrients—important for environmental sustainability of microalgae production.

The current commercial methods for harvesting microalgae include centrifugation, filtration, and flocculation followed by settling or dissolved air flotation. Centrifugation can produce thick pastes with high solids concentration (~20% (w/w)), and this method also allows for recovery of uncontaminated culture media for recycling. Recently, microalgae-specific low-speed centrifuges have been developed by Evodos™ that require less energy (8 kWh/m$^3$ of media processed) than more conventional centrifuges used in the biotechnology and fermentation industries. Cell lysis can also be prevented in the Evodos™ models. Nonetheless, the capital costs associated with centrifugation are unappealing.

Cross flow filtration is another method that has primary use in biotechnology/fermentation, but could also be applied for separation of microalgae. With this technique, reasonably high biomass concentrations can be achieved (8% (w/w)), and since no chemicals are added in this process, the recovered permeate can be recycled. When solids concentrations are low, such as in microalgae cultures from open raceway ponds, the energy use is also low due to small cake resistance (approximately 2 kWh/m$^3$). However, the primary concern with cross flow filtration is the cost associated with membrane replacement and membrane cleaning. Due to the presence of exo-polysaccharides in many algal cells, irreversible fouling of membranes is unavoidable in commercially available 0.22 µm cross flow filtration modules, necessitating frequent membrane replacements. Fouling issues could be avoided, at least in part, by use of membranes with larger pore sizes (3-5 µm). However, low-cost large-pore membrane modules are not commercially available and may be challenging to manufacture since conventional polymer membrane supports have sub-micron pore sizes.

Flocculation followed by settling or dissolved air flotation, adapted from wastewater treatment, can also be used for harvesting microalgae. With this technique too, reasonably high slurry concentrations can be achieved (5-10% (w/w)) with energy consumption varying between 10-20 kWh/m$^3$. However, addition of flocculants precludes the recycling of growth media for microalgae re-cultivation. Also, the carryover of flocculants with the harvested biomass could negatively impact downstream conversion processes and fuel quality.

Historical observations have shown that some microalgae species are also able to "autoflocculate" under alkaline conditions. Investigations to elucidate the mechanism for this occasional spontaneous settling of microalgal cells show that the process might actually be a result of chemical flocculation due to precipitation of calcium and magnesium hydroxides (from Ca and Mg salts in the growth media) when solution pH is high. Further, this process results in only a small increase in concentration of cells (up to 0.1 to 0.5%). Secondary harvesting methods are therefore still needed to increase concentrations to levels compatible with conversion processes (~10% (w/w)). In any case, auto flocculation appears to be species-specific and this method is likely applicable only to a few select strains.

It is clear that while harvesting methods from other industries may be applied to microalgae cultures, they are not particularly well-suited. Cross flow filtration and centrifugation are best suited for biotechnology applications with high cell concentrations of fermentation cultures and a high value of the products. Flocculation works well in wastewater treatment since recyclability of water and quality of recovered biomass are not of primary concern. Clearly, transformative alternatives for dewatering dilute microalgae slurries are still needed.

SUMMARY OF THE INVENTION

Provided is a harvesting device comprising a first end having a first opening in communication with a jacket, and a second end having a second opening in communication with an inner chamber, where the jacket at least partially surrounds the inner chamber. The harvesting device further includes a first valve configured to control flow of a fluid into the jacket from the first opening, and a second valve configured to control flow of a liquid into and out of the inner chamber through the second opening. The harvesting device further includes a central tube extending through the inner chamber and in communication with the second opening, and at least one bucket within the inner chamber having a horizontal mesh defining a bed, where the bucket is disposed adjacent to the central tube. A plurality of one-way check valves are configured to allow passage of a fluid from the jacket into the inner chamber, and the central tube has perforations configured to allow passage of a substance between the central tube and the bucket. In certain embodiments, the bucket circumferentially surrounds the central tube.

In certain embodiments, the harvesting device includes a plurality of buckets. In certain embodiments, one or more of the jacket, the inner chamber, or the central tube is annular. In certain embodiments, the inner chamber is concentric with the central tube. In certain embodiments, the jacket is concentric with the central tube. In certain embodiments, the harvesting device further includes a pump connected to the second opening. In certain embodiments, the harvesting device further includes a gas source connected to the first opening. In certain embodiments, the harvesting device further includes a heat source configured to heat a fluid administered into the first opening.

In certain embodiments, the horizontal mesh holds segments of a hydrogel. In particular embodiments, the hydrogel is a stimuli-sensitive hydrogel. In particular embodiments, the hydrogel is a semi-IPN hydrogel. In particular embodiments, the hydrogel comprises PNIPAAm.

Further provided is a method of using the harvesting device, the method including the steps of filling the bed with a stimuli-sensitive hydrogel; introducing dilute algal cultures in a culture media onto the bed through the central tube; closing the second valve; allowing the hydrogel to absorb the culture media and swell, thereby creating a concentrated algal slurry in the inner chamber; and opening the second valve to remove a concentrated algal slurry from the harvesting device. In certain embodiments, the stimuli-sensitive hydrogel comprises a semi-IPN hydrogel. In certain embodiments, the method further includes the steps of introducing a stimulus into the jacket through the first valve so as to force open the one-way check valves and introduce the stimulus into the inner chamber, where the stimulus causes the swollen hydrogel to deswell and release media; and removing the released media from the harvesting device through the second valve. In particular embodiments, the stimulus is heat or $CO_2$.

Further provided is a method for harvesting algae, the method including the steps of immersing a stimuli-sensitive hydrogel in a liquid containing algae at a first concentration; allowing the stimuli-sensitive hydrogel to absorb the liquid for a first period of time, thereby forming a swollen hydrogel; and removing algae at a second concentration from the liquid, where the second concentration is greater than the first concentration. In certain embodiments, the method further includes the step of introducing a stimulus to the swollen hydrogel to form a deswollen hydrogel and release absorbed liquid. In particular embodiments, each step is repeated in one or more cycles. In particular embodiments, introducing the stimulus involves heating the stimuli-sensitive hydrogel. In particular embodiments, introducing the stimulus involves decreasing the pH of the liquid. In certain embodiments, the stimuli-sensitive hydrogel is a semi-IPN hydrogel. In certain embodiments, the stimuli-sensitive hydrogel is selected from the group consisting of: a temperature-sensitive hydrogel, a pH-sensitive hydrogel, a light-sensitive hydrogel, an electric field-sensitive hydrogel, an ion-sensitive hydrogel, a pressure-sensitive hydrogel, and a molecule-sensitive hydrogel. In certain embodiments, the first period of time is from about 30 minutes to about 2 hours. In certain embodiments, the second period of time is from about 30 minutes to about 2 hours. In certain embodiments, the swollen hydrogel is only partially swollen.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIG. 1B—Step 1: Dilute algae solution is introduced into the inner chamber through the second opening. The check valves connected to the jacket are kept closed to prevent leakage of algae slurry into the jacket. FIG. 1B—Step 2: Concentrated algae solution is removed from the inner chamber, leaving behind swollen hydrogels containing absorbed growth media. The check valves connected to the jacket remain closed. FIG. 1B—Step 3: Heat or $CO_2$ is introduced into the jacket through the first opening. The check valves on the jacket are forced open, allowing the heat or $CO_2$ to enter into the inner chamber. These stimuli cause deswelling of the swollen hydrogels. The desorbed growth media is drained through the second opening. FIG. 1B—Step 4: Hydogels are fully shrunken and the first valve is closed. The inner chamber has been fully drained and is ready for re-introduction of dilute algae feed.

(FIG. 3A.) Aqueous media uptake and release performance of PNIPAAm hydrogels when subjected to successive swelling-deswelling cycles. (FIG. 3B.) The solid and dashed lines in FIG. 3B represent the swelling and deswelling portions of each cycle, respectively.

FIG. 11A shows the storage modulus (G') of the hydrogels without compression (3 mm plate gap). FIG. 11B shows the G' values of compressed hydrogels (2 mm plate gap). The G' curves of compressed fully-swollen and partially-swollen PNIPAAm hydrogels are very similar and overlap.

Values indicate average of duplicate 3-stage runs. Error bars represent one standard deviation from mean values.

Figure 13:
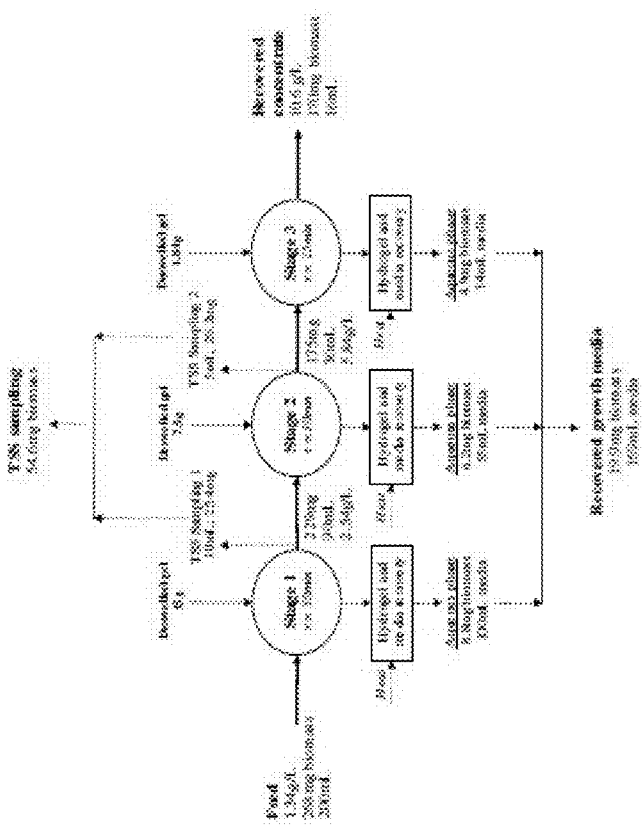

FIG. 13: First experimental run of a stage-wise concentration of microalgae cultures using PNIPAAm hydrogels.

Figure 14:
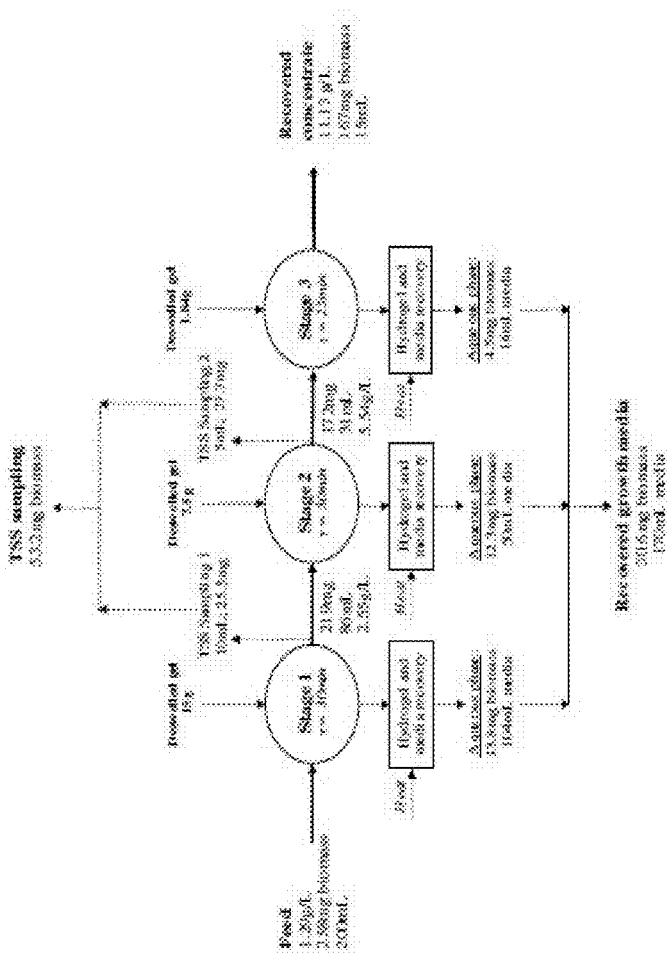

FIG. 14: Second experimental run of a stage-wise concentration of microalgae cultures using PNIPAAm hydrogels.

Figure 15:
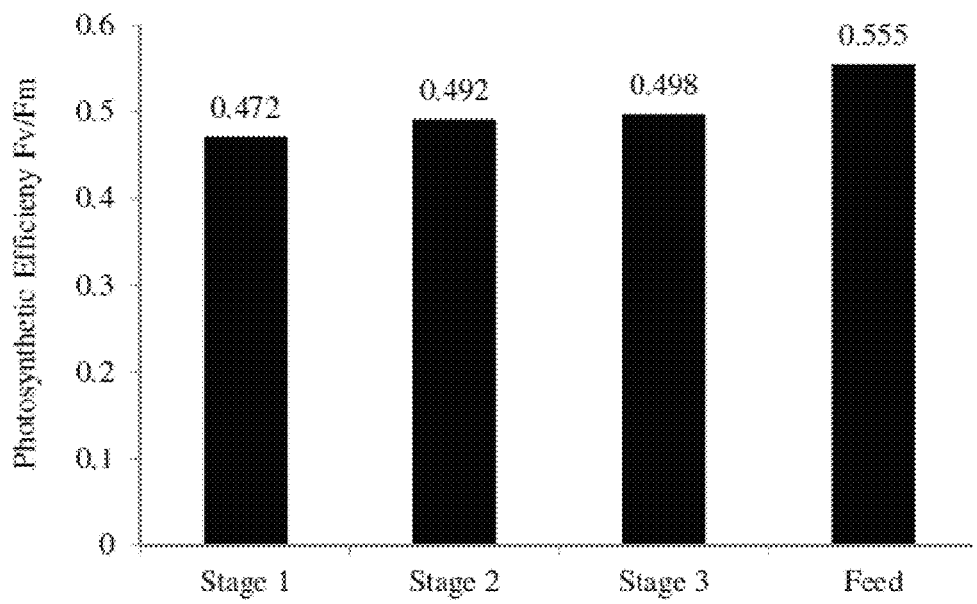

FIG. 15: Photosynthetic efficiency changes for recovered medium and dilute feed culture.

Figure 16:
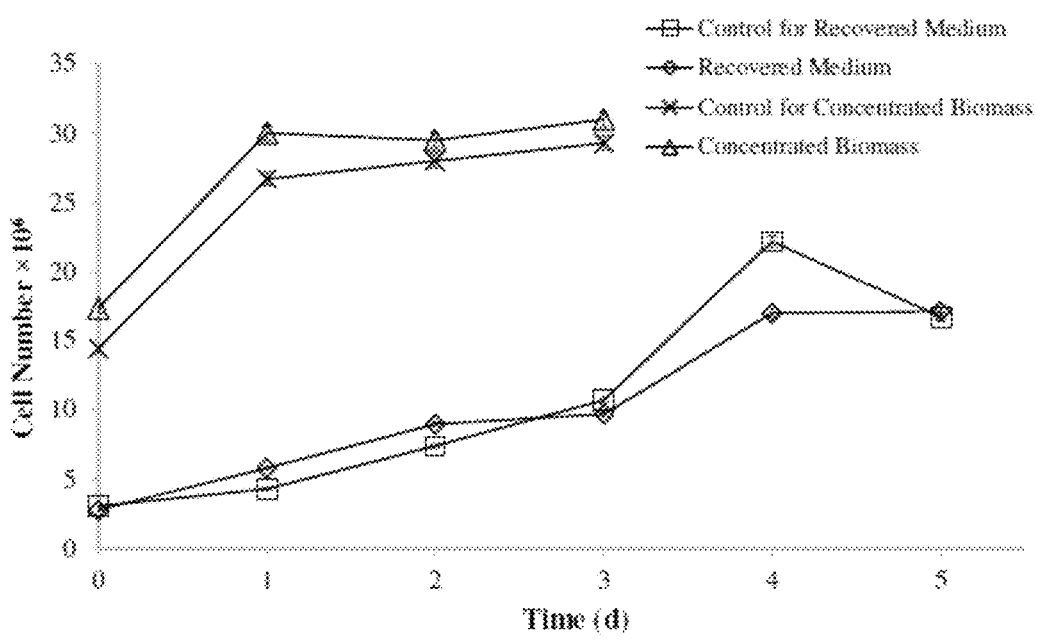

FIG. 16: Cell number changes during growth of re-cultivated samples.

Figure 17A:
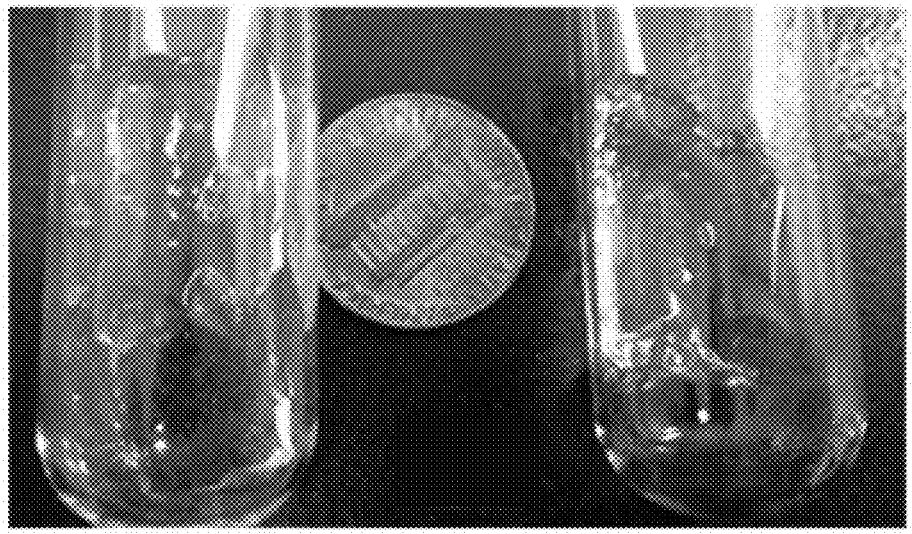
Figure 17B:
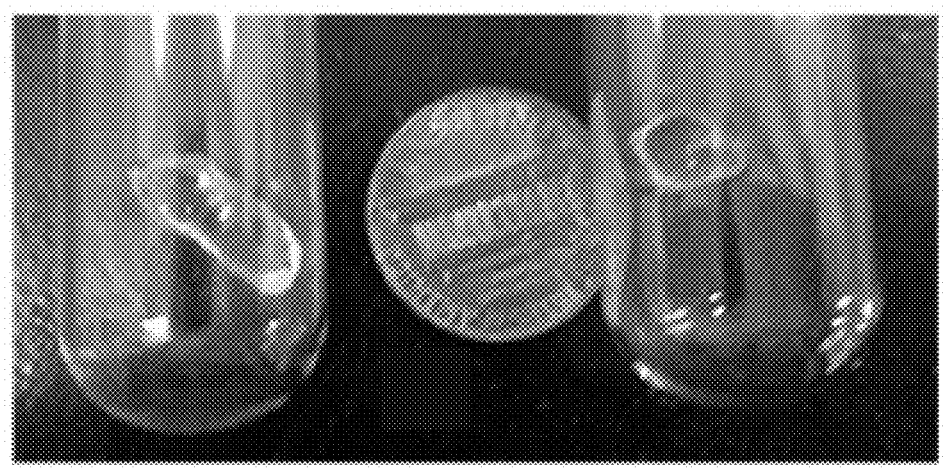

FIGS. 17A-17B: Swollen PAA hydrogels (FIG. 17A) and PAA hydrogels deswollen with $CO_2$ (FIG. 17B). The penny is shown for size reference.

Figure 18:
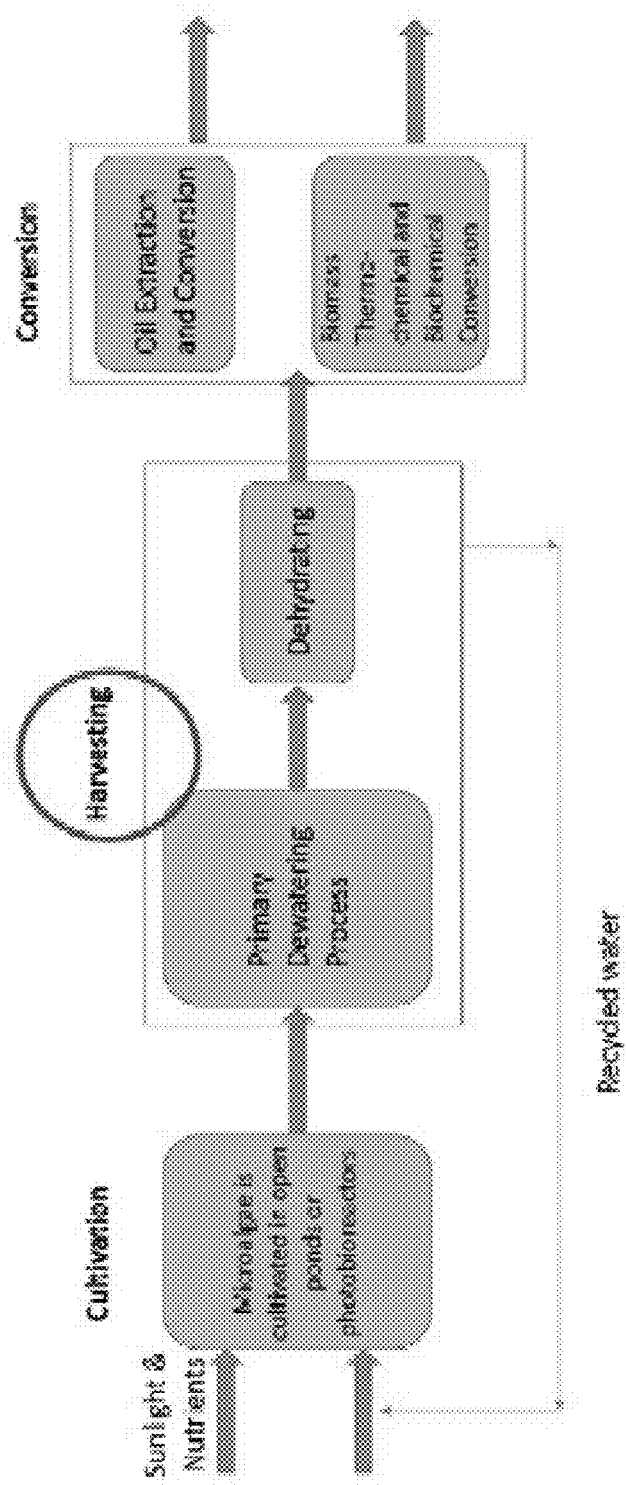

FIG. 18: Schematic of a microalgae biorefinery process.

DETAILED DESCRIPTION OF THE INVENTION

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

A low-energy technology for harvesting microalgae through the use of stimuli-sensitive hydrogels has been developed. As shown in the examples herein, it has been demonstrated that microalgae concentrations can be increased to >100 g/L using a multi-stage approach. Further, it has been demonstrated that by using appropriate combinations of gel type, gel loadings, and residence time per stage, the overall process time can be minimized. It has also been demonstrated that the microalgae cells and media recovered from the hydrogel harvesting process are unspoiled; cells remain viable and can be re-cultivated, while the media can be recycled to support additional algae growth.

A constraint with using soft materials such as hydrogels for commercial-scale applications (e.g. biofuels) is loss of mass and properties due to mechanical disruption of the hydrogels. However, provided herein is a harvesting device that minimizes exposure of gel to mechanical attrition and preserved longevity. The harvesting device also allows easy integration of low-quality waste heat or $CO_2$, such that energy costs associated with harvesting are minimized.

Figure 1A:
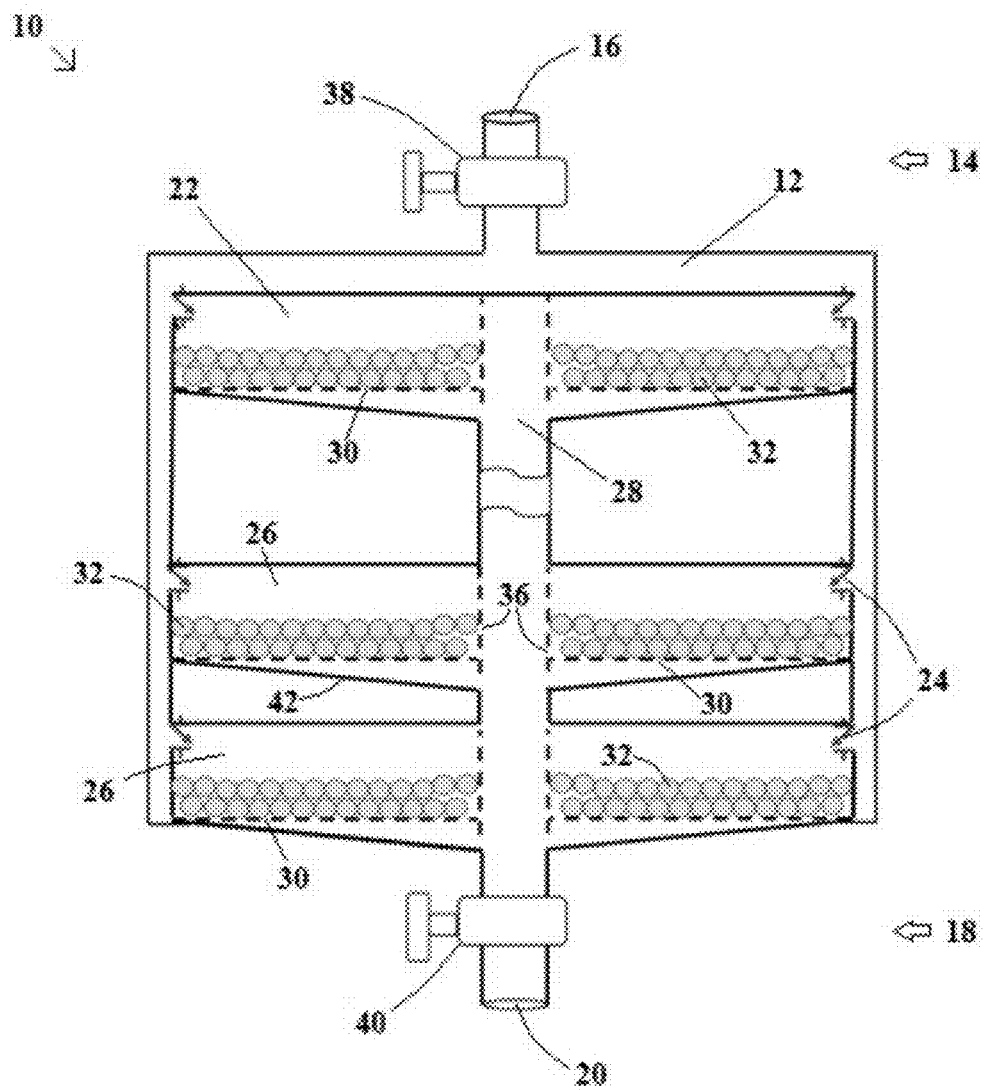
FIGS. 1A-1B: Schematic illustration of the hydrogel-based algae harvesting device (FIG. 1A) and schematic illustration of a non-limiting example of a stepwise process of using the hydrogel-based algae harvesting device (FIG. 1B, showing Steps 1-4, from left to right). The light green color in FIG. 1B signifies a low concentration of algae present, and the darker green color in FIG. 1B signifies a higher concentration of algae present.

Referring now to FIG. 1A, the harvesting device 10 generally includes a first end 14 having a first opening 16 in communication with a jacket 12, and a second end 18 having a second opening 20 in communication with an inner chamber 22. The jacket 12 at least partially surrounds the inner chamber 22. In some embodiments, the jacket 12 completely surrounds and houses the inner chamber 22. Passage of substances through first opening 16 is controllably allowed or prevented by a first valve 38, and passage of substances through the second opening 20 is controllably allowed or prevented by a second valve 40. The jacket 12 is configured to deliver a fluid, such as steam, a hot gas, or $CO_2$ from the first opening 16 into the inner chamber 22 via a series of one-way check valves 24.

Inside the inner chamber 22, one or more buckets 26 (also referred to as trays) are stacked, in some cases in segments of two (as depicted in FIG. 1A), at least partially adjacent to a central tube 28, which extends throughout the inner chamber 22 and protrudes out the second end 18 through the outlet 20. In some embodiments, the buckets 26 are stacked circumferentially around the central tube 28 so as to completely surround the central tube 28. Each bucket 26 contains a horizontal mesh 30 which forms a bed onto which gel segments 32 can be placed. In this context, the term "horizontal" means about perpendicular to the axis defined by the central tube 28. It is understood that the horizontal mesh 30 is referred to as such for purposes of clarity, but in fact need not be truly horizontal with respect to any particular reference point. The horizontal mesh 30 can be made of any suitable material having perforations or pores large enough for algae cells to pass through but small enough that the gel segment 32 do not pass through. The gel segments 32 are arranged on the horizontal mesh 30 so as to allow for steam and heat to move sufficiently throughout the inner chamber 22, and also to allow enough space for the gel segments 32 to expand upon swelling. The buckets 26 can have a sloped bottom surface 42 underneath the horizontal mesh 30.

The central tube 28 has perforations 36 that allow passage of substances between the beds and the inside of the central tube 28. The central tube 28 is in direct communication with and/or forms the second opening 20. The central tube 28 can drain media from the harvesting device 10 through the second opening 20 with the aid of gravity or a pump. The central tube 28 can also deliver media into the inner chamber 22 of the harvesting device 10 with the aid of a pump. When pumped in, the media flows out radially from the central tube 28 into the buckets 26 and onto the beds. The second valve 40 can be utilized to prevent flow of media from inside the inner chamber 22 to outside the harvesting device 10 through the second opening 20. The first valve 38, on the other hand, controls access of a fluid into the jacket 12. When a fluid is delivered into the jacket 12 via the first opening 16, the fluid can travel through the one-way check valves 24 into the inner chamber 22. The first opening 16 does not communicate directly with the central tube 28. Thus, the first opening 16 is configured for entry of a fluid into the harvesting device 10, while the second opening 20 is configured for exit of a liquid or slurry from the inner chamber 22 to outside the harvesting device 10, or for entry of a liquid or slurry from outside the harvesting device 10 into the inner chamber 22. The fluid communication between the jacket 12 and the inner chamber 22 is provided only by the one-way check valves 24.

The harvesting device 10 can, but need not, be annular. In one non-limiting example, the jacket 12, inner chamber 22, and central tube 28 are all concentric. In other embodiments, the harvesting device 10 is annular but two or more of the jacket 12, inner chamber 22, and central tube 28 are not concentric. In some embodiments, one or more of the jacket 12, inner chamber 22, and central tube 28 is rectangular or elliptical. Furthermore, the positioning of the buckets 26 around the central tube 28 need not be circumferential, though circumferential positioning of the buckets 26 around the central tube 28 provide for a radial and even distribution of media to the beds when delivered through the central tube 28.

The gels used in the harvesting device 10 are generally hydrogels. More specifically, the gels are generally stimuli-sensitive hydrogels. Hydrogels are superabsorbent, hydrophilic, cross-linked polymers that can absorb and hold large quantities of water and "swell" in aqueous solutions. Stimuli-sensitive hydrogels absorb and release water in response to an external stimulus. That is, stimuli-sensitive hydrogels can also "de-swell" (i.e., release the absorbed water) based on an external stimulus. Many different kinds of stimuli-sensitive hydrogels exist and are suitable for the present disclosure. For instance, hydrogels can be sensitive to temperature, pH, light, ions, electric fields, pressure, or specific molecules. The present disclosure further describes the use of temperature-sensitive hydrogels and pH-sensitive hydrogels for exemplary purposes, but any stimuli-sensitive hydrogel can be utilized in conjunction with the appropriate stimulus.

Temperature-sensitive polymers, such as poly(N-isopropyl acrylamide) (PNIPAAm), swell at room temperature but show a large volume change (deswell) as they undergo a phase transition when heated above their lower critical solution temperatures (LCST). The LCST for PNIPAAm is 32° C., but can be increased or decreased based on co-polymerization with hydrophilic or hydrophobic co-monomers. The swelling kinetics of PNIPAAm gels can also be improved through intercalation of additional polymers such as poly(vinyl alcohol) into the PNIPAAm gel structure.

pH-sensitive gels can be made from weak polyacids such as poly(acrylic acid) (PAA). At solution pH values close to the $pK_a$ of the polyacids (pH*), the polymer becomes protonated and transitions to a more hydrophobic form which results in expulsion of water from the hydrogel (referred to as deswelling). At pH values higher than pH*, the hydrophilic polymers readily absorb water and swell. Although monomeric acids have $pK_a$ values of 4-5, the polyacids have typically a higher $pK_a$ ($pK_a$=5 to 6) due to the local electrostatic environment. The phase transition pH values can also be increased (pH*>6) by co-polymerization of the weak acids with alkylated acid monomers (e.g. co-polymerization of acrylic acid with alkylated acrylic acid). Near-neutral pH swings can be accomplished using controlled $CO_2$ addition (sparging), though other acidic stimulants can be utilized to accomplish this task. Finally, PAA derivatives containing hydrophobic groups, such as poly(methacrylic acid) (PMAA) and poly(propylacrylic acid) (PPAA), exhibit a sharper phase transition.

Some stimuli-sensitive hydrogels are poly-(N-isopropylacrylamide)/polyvinyl alcohol (PNIPAAm-PVA) semi-interpenetrating (semi-IPN) networks, which are composed of one cross-linked polymer and one polymer in linear form. These polymers are interlaced on a molecular scale without chemical bonds. These semi-IPN gels generally have increased mechanical strength, improved longevity during prolonged reuse, better malleability and toughness, increased hydrophobicity, and better swelling kinetics without changes in LCST or thermoresponsive properties. Semi-IPN gels swell quicker and de-swell quicker than other hydrogels. Therefore, semi-IPN gels are particularly useful in the present disclosure, but are not necessary.

Other stimuli-sensitive hydrogels can be utilized in the present disclosure. Monomers suitable for polymerizing into other stimuli-sensitive hydrogels include, but are not limited to, acrylates, acrylamides, acetates, acrylic acids, vinyl alcohols, and glycols. Furthermore, some hydrogels break more easily when fully swollen. Partial swelling improves the strength of the hydrogels. Therefore, in some embodiments, the hydrogels are only partially swollen before being de-swollen. As the examples herein show, hydrogels are actually strong enough to require a depth of about 30 feet of water above them before they would be crushed by the water.

Without wishing to be bound by theory, it is believed that hydrogels are effective at concentrating algae solutions because hydrogels have pores that are too small to imbibe algae cells; thus, the hydrogels absorb water but exclude algae. If needed, the pore size of a hydrogel can be adjusted by changing the crosslinker density. In general, there are smaller pores with more crosslinks present in the gel.

A stimuli-sensitive hydrogel-based method to selectively absorb aqueous media from microalgal suspensions and thereby increase the concentration of algal slurries can be practiced with or without the particular harvesting device described herein. When stimuli-sensitive hydrogels are immersed in microalgae cultures at ambient conditions, they "soak-up" large quantities of culture media while microalgae cells are rejected due to the small size of gel pores. This preferential uptake of the aqueous phase results in an increase in biomass concentration in the culture. After absorbing growth media, the swollen hydrogels can be easily recovered and de-swelled by applying a stimulus—for example, (1) temperature-sensitive pNIPAAm gels de-swell when subjected to a small increase in temperature (>33° C.), and (2) pH-sensitive polyacrylic acid or poly methacrylic hydrogels deswell when pH is lowered to values less than 5-6. Without wishing to be bound by theory, it is believed that most of the algae particles that become stuck to the surface of the swollen gels are released with the force of the released water upon deswelling. The de-swelled hydrogels can then be re-used to absorb more medium. If any algae particles remain stuck to the surface of the gels, they can be recovered and regrown for cultures.

Hydrogel materials are relatively inexpensive and also have high swelling ratios (i.e., the ratio of water absorbed to the mass of hydrogel polymer)—typically more than 20. Due to reuse of the stimuli-sensitive hydrogels, only small amounts of gel are ultimately needed to absorb very large volumes of media, which further reduces the cost associated with purchase/replacement of these materials. The examples herein show that hydrogels can be re-used for greater than 6 months without any measurable loss in performance.

The examples further show that the hydrogel harvesting method can be used to increase biomass concentrations from 0.1% to nearly 10% without loss of algae quality. At these concentrations, the slurries can be further concentrated using more conventional and commercially available methods, or used directly in downstream conversion processes. Finally, the hydrogel dewatering technology is insensitive to the microalgae species being harvested since the method relies on physical absorption of the culture medium and does not rely on the cell properties such as surface charge or specific gravity of the cells.

Figure 1B:
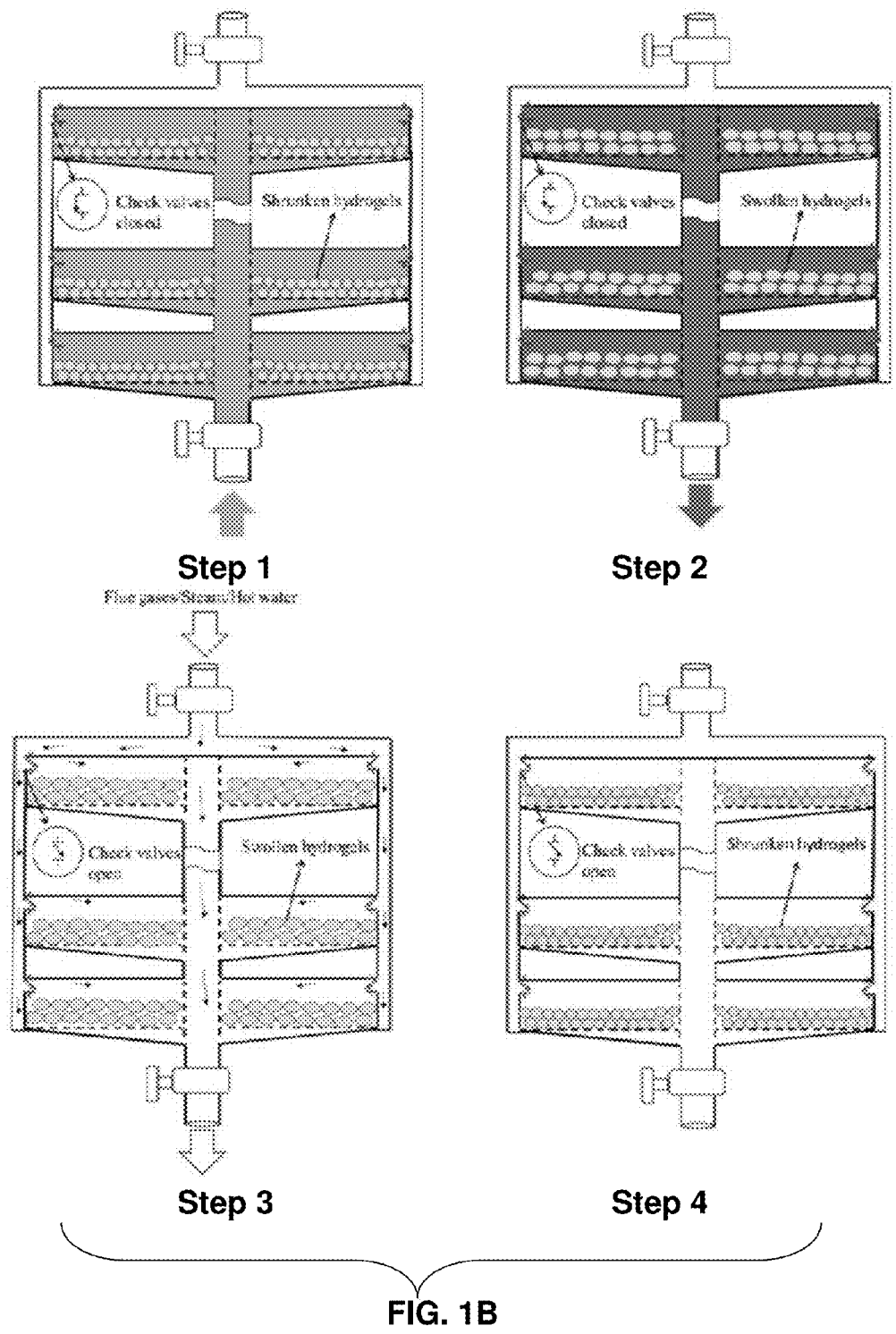

A key challenge in implementing a commercial-scale hydrogel-based process is constructing a harvesting device that can minimize loss of hydrogel due to mechanical attrition or breakage. In addition, such a device should be scalable and allow continuous operation. The harvesting device described, shown in FIGS. 1A-1B, meets these objectives. Again referring to FIG. IA, the harvesting device 10 includes a stack of semi-conical buckets 26 with a horizontal mesh 30 (depicted in FIGS. 1A-1B as a dashed horizontal line) that hold the gel segments 32. The height of each bucket 26 is designed to just-accommodate swollen gels to maximize use of the available volume. The central tube 28 delivers microalgae slurries in and out of the gel beds through perforations 36 (depicted in FIGS. 1A-1B as dashed lines). The second valve 40 at the bottom of the central tube 28 (i.e., the second end 18 of the harvesting device 10) controls the timed movement of fluids in and out of the device. The beds can be a of a "clam shell" design to allow replacement of gels, if needed or desired. Overall, the device can minimize or eliminate the movement of gel segments 32 and avoid attrition of the gels.

The jacket 12 around the inner chamber 22 is for the purpose of introducing hot fluids (steam, hot water, or other hot gases) or $CO_2$. These fluids provide the stimuli for the hydrogels to transition from swollen to shrunken (that is, deswollen) state by temperature-shift (with hot fluids) or pH-shift (with $CO_2$), and release the absorbed aqueous media. The deswelling fluids are injected into the harvesting device 10 through the first opening 16 connected to the jacket 12 and then enter the internal buckets 26 through the one-way check valves 24 to contact the gel segments 32 disposed on the beds and thereby facilitate the deswelling process. The flow of fluids into the first jacket 12 can be controlled by the first valve 38.

In step 1 of a stepwise operation of the harvesting device, dilute algal cultures are introduced into the gel beds through the central tube 28. For optimal results, the gel segments 32 are completely submerged when the harvesting device 10 is filled with algae media. The harvesting device 10 can be scaled up to house a media depth of about 10 meters without significant risk of damage to the submerged gels.

After the beds are filled, the second valve 40 is closed and the gels 32 are allowed to absorb the culture media and swell. The check valves 24 connected to the jacket 12 are forced closed by the liquid inside the inner chamber 22 pushing against the valves 24. The closed check valves 24 prevent leakage of microalgae slurry into the surrounding jacket 12. At the end of the swelling period, in Step 2, the second valve 40 is opened to drain (through the second opening 20) and recover the concentrated algal slurry produced as a result of preferential absorption of the aqueous medium. In Step 3, heat or $CO_2$ is introduced into the jacket 12 through the first opening 16. The check valves 24 on the jacket 12 are forced open, allowing the hot fluids/$CO_2$ to enter into the inner chamber 22. For pH sensitive gels, $CO_2$-rich gases serve to reduce the pH. These stimuli cause deswelling of the swollen hydrogels. The desorbed growth media is drained though the second opening 20. In Step 4, hydrogels are fully shrunken and the first valve 38 is closed. At this point, the inner chamber 22 has been fully drained and is ready for re-introduction of dilute microalgae feed.

Preferably, the dewatering is conducted to concentrate algae to a concentration of about 100 g/L. This concentration produces a paste that is especially suitable for drying and processing. With the harvesting device, continuous harvesting can be achieved with parallel units using timed operations similar to those used in pressure swing adsorption systems. Further, the hydrogels stay immobile while fluids are circulated in and out of the harvesting device. This prevents attrition of gels that would occur if the hydrogels were transported instead. In addition, due to the distribution of gels over multiple beds, mechanical crushing and rupture of gels under their own weight is avoided. The short stacks also allow gels to expand freely during swelling without pushing against excessive surrounding gel mass, and the multiple trays/beds permit uniform and efficient heat (or $CO_2$) transfer to the gels during deswelling.

The central tube 28 connected to the gel trays 26 distributes fluids (dilute and concentrated slurries as well as utility fluids) through the harvesting device 10 without excess pressure drop, and without associated mechanical stress on the hydrogels. In addition, the external jacket 12 introduces deswelling fluids throughout the device efficiently. Finally, the buckets 26 can have a sloped bottom 42 that facilitates easy drainage of concentrated slurries and recovered media after the swelling and deswelling steps, respectively.

Thus, the harvesting device addresses the primary challenge of hydrogel based separation systems—hydrogel handling. In designs that would rely on physical movement of gels through static aqueous solutions, gel loss through attrition and physical damage of these soft materials would be unavoidable. Overall, the harvesting device allows for efficient size-based separation, efficient heat and mass transport, and maintenance of gel integrity for prolonged use. The device and methods described are useful for the production of a multitude of algae-based biofuels and bioproducts, such as high-value nutraceuticals (for example, omega fatty acids or astaxanthin), on a commercial scale. The present disclosure can, for example, be employed as the primary dewatering process of a microalgae bio-refinery process such as that illustrated for exemplary purposes in FIG. 18.

EXAMPLES

Example 1

Swelling Kinetics of Poly-N-Isopropylacrylamide (PNIPAAm) Hydrogels in the Presence and Absence of Microalgae To prepare PNIPAAm hydrogels, first, 7.92 g of N-isoproprylacrylamide, 80 mg of N,N'-methylenebisacrylamide, and 5 mg of ammonium persulfate were dissolved in 100 mL of de-ionized (DI) water. This solution was then transferred to a glass tube (2.5 cm dia. and 15 cm long) with one end sealed, and flushed with $N_2$ for 5 min to purge the dissolved $O_2$. Then, 5 mg of sodium meta-bisulphate was added and the solution was again flushed with $N_2$. At this stage, the other end of the glass tube was also sealed and the polymerization reaction was allowed to proceed for 1 h at room temperature.

Once the polymerization reaction was completed, a clear transparent gel was formed in the tube. The gel was removed from the tube and washed for 48 h with DI water in order to remove any unreacted monomer and cross-linker. After washing, the gel was cut into 10 mm×8 mm×5 mm pieces which were frozen for 24 h at −20° C. The frozen gel pieces were then thawed and dried in an oven, before examining their swelling/deswelling kinetics.

*Chlorella* sp. cultures for dewatering experiments were cultivated under continuous illumination, stirring, and air sparging in 3 L Cytostir® spinner flask reactors (Kimble/Kontes, Vineland, N.J., USA). The growth medium contained $NaNO_3$ (0.25 g/L), $NH_4Cl$ (0.05 g/L), $MgSO_4.7H_2O$ (0.075 g/L), $CaCl_2.2H_2O$ (0.0 g/L), NaCl (0.025 g/L), ferric ammonium citrate $C_6H_{5+4y}Fe_xN_yO_7$ (0.01 g/L), $K_2HPO_4$ (0.25 g/L), $Na_2CO_3$ (0.25 g/L), and trace element solution (1 mL/1 L-medium). Biomass concentration during culture growth was determined by measuring total suspended solids (TSS) concentration (described later).

After cultures reached stationary phase (concentration of 1.6 g/L), a portion of the cultures was centrifuged (3000×g) and the obtained pellet was re-suspended in fresh media to obtain slurries of various concentrations.

Figure 2:
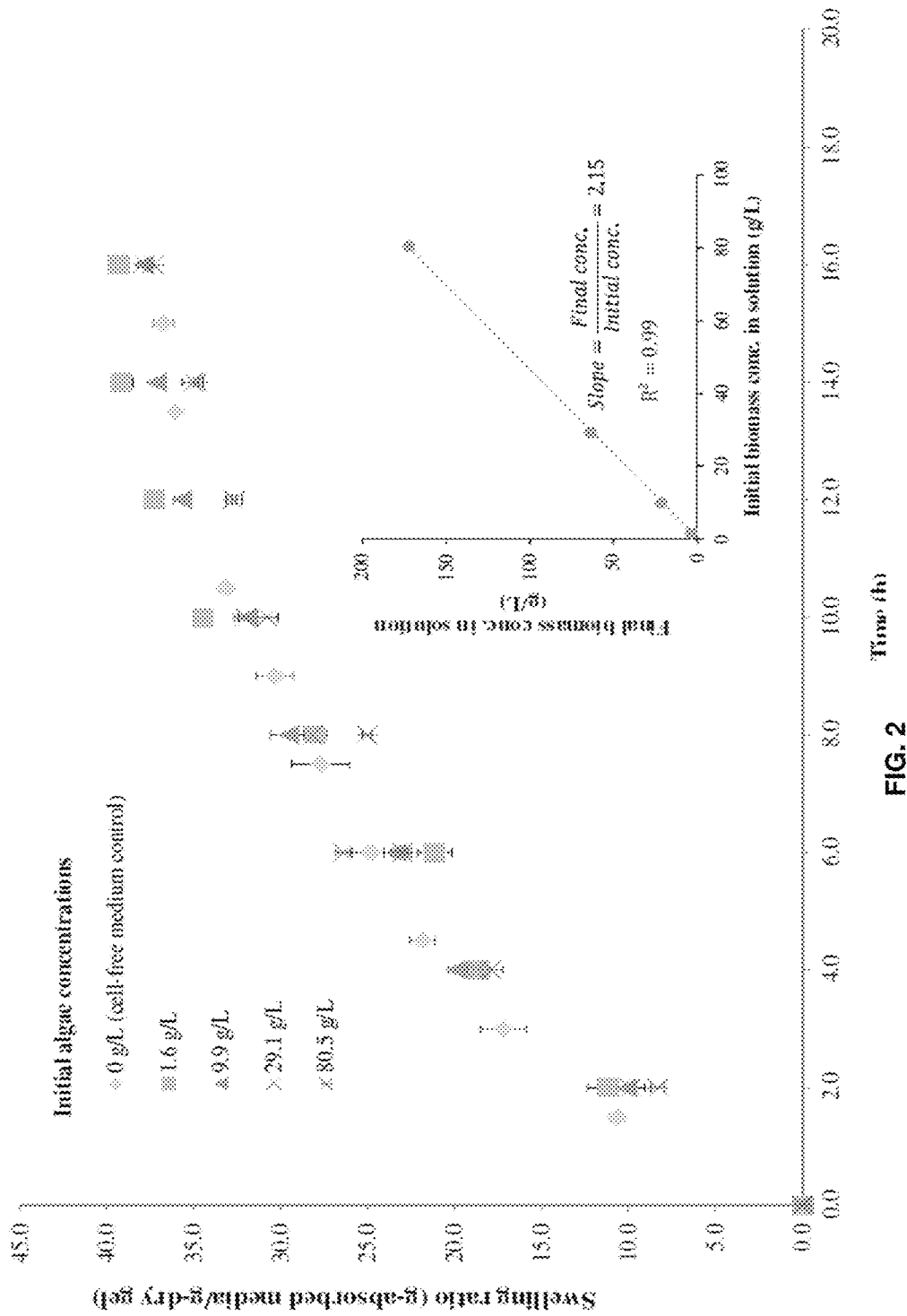
FIG. 2: Swelling performance of hydrogels in microalgae slurries. Inset shows the correlation between cell concentrations before and after incubation of microalgae slurries with hydrogels. Results show that the rates of water absorption were not influenced by the presence of microalgae cells even at very high concentrations of >80 g/L.

Hydrogels were swollen in these variously concentrated microalgae slurries as well as in cell-free media. 0.5 g of dry hydrogel was added to the aqueous solutions and incubated at room temperature (20° C.). Swelling kinetics of hydrogels incubated in cell-free media were measured directly though gravimetric analysis by periodically removing the hydrogels and measuring their weight. In addition, for the experiments that incubated hydrogels with microalgae slurries, the concentrations of microalgae biomass in free aqueous solution (not absorbed by the hydrogels) were also periodically monitored. Due to the uptake of aqueous media by the hydrogels, the suspended cell concentrations in these cultures increased over time. The volume of media absorbed by the hydrogels was then estimated based on the increase in cell concentrations. Thereafter, hydrogel swelling ratios were calculated by dividing the mass of absorbed media by the dry gel weight. The changes in swelling ratio of the hydrogels incubated in the presence and absence of microalgae cells is shown in FIG. 2. From these results, it can be seen that the hydrogel swelling rates in dilute (1.6 g/L) as well as concentrated cultures (80.4 g/L) were estimated to be very similar and also closely matched with the measured swelling ratios in cell-free media. These results indicated that gel performance was not affected by the presence of algae, and occlusion of gel pores by algal cells, if any, is insignificant. Also, after slurries were dewatered, final biomass concentrations in all cases were increased by a factor of approximately 2.15, as evident from the slope of the linear correlation shown in the inset to FIG. 2. These results further confirm that absorption of aqueous solutions by the hydrogels was not affected by the presence of algae cells over the wide biomass concentration range of 1 g/L to 160 g/L.

Example 2

PNIPAAm Swelling and Deswelling Performance During Cyclic Reuse

For these experiments, the PNIPAAm hydrogels were prepared using a protocol similar to Example 1, but the gels were cut into smaller pieces (3 mm×3 mm×3 mm) To determine swelling kinetics, dry gels were added to water or algae growth media and incubated at room temperature for 24h. Uptake of growth media by hydrogels was quantified by gravimetrically monitoring swollen gel weights. Before starting the experiment, prepared hydrogel pieces were dehydrated in an oven at 40° C. 0.5 g of dry gel pieces were weighed at room temperature, placed on a sheet of nylon mesh (approximately 6 cm in diameter) of known weight and incubated in fresh growth medium (composition of the growth medium is described later). As the hydrogels swelled, the nylon mesh along with the enclosed hydrogels was periodically removed and weighed. Before weighing, the free liquid (around the hydrogel pieces) was allowed to drain by gravity and the outside of the mesh was dabbed with moist paper towels to remove any additional external liquid. Swollen gel weights were measured using an analytical balance (Shimadzu AUW120D, Kyoto, Japan; max: 120 g, min: 1 mg; accuracy: d=0.1 mg). Hydrogels were allowed to swell until nearly-constant gel weight was achieved.

Thereafter, the hydrogels were recovered and incubated in an oven at 37° C. for 4h to deswell the gels and release the absorbed aqueous media. During the deswelling process also, gels were periodically weighed until constant weight was achieved.

Figure 3A:
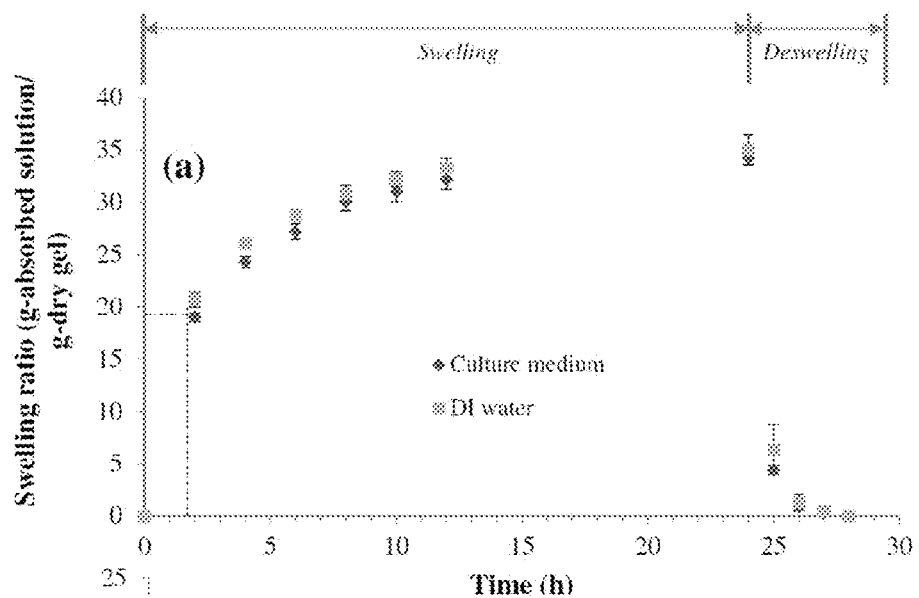
FIGS. 3A-3B: Swelling and deswelling kinetics of PNIPAAm hydrogels in DI water and microalgae culture media.

As a result of a larger surface area (due to smaller-sized gels) in contact with the solution, these gels swelled at a faster rate than the hydrogels that were previously used for experiments described in Example 1 (compare swelling rates in FIG. 3A with FIG. 2). Highest swelling rates were obtained during the initial period of incubation and swelling ratios of nearly 20 g-absorbed solution/g-dry gel were obtained in 0-2h. Equilibrium swelling ratios of nearly 35 g-absorbed solution/g-dry gel were obtained after much longer incubation (>12h). These results indicated that the harvesting process would be most expeditious if short swelling periods are employed (2h or less) to rapidly absorb the aqueous solutions, rather than awaiting equilibrium. Longer residence times would allow lower use of gel per stage, but savings in gel cost may not be significant in this approach if gel recycle is effective. In addition, the short swelling period would also match the deswelling time to release most of the absorbed media (approx. 2h; see deswelling curve in FIG. 3A) such that swelling and deswelling operations could be carried out in parallel akin to commercial pressure-swing adsorption.

Figure 3B:
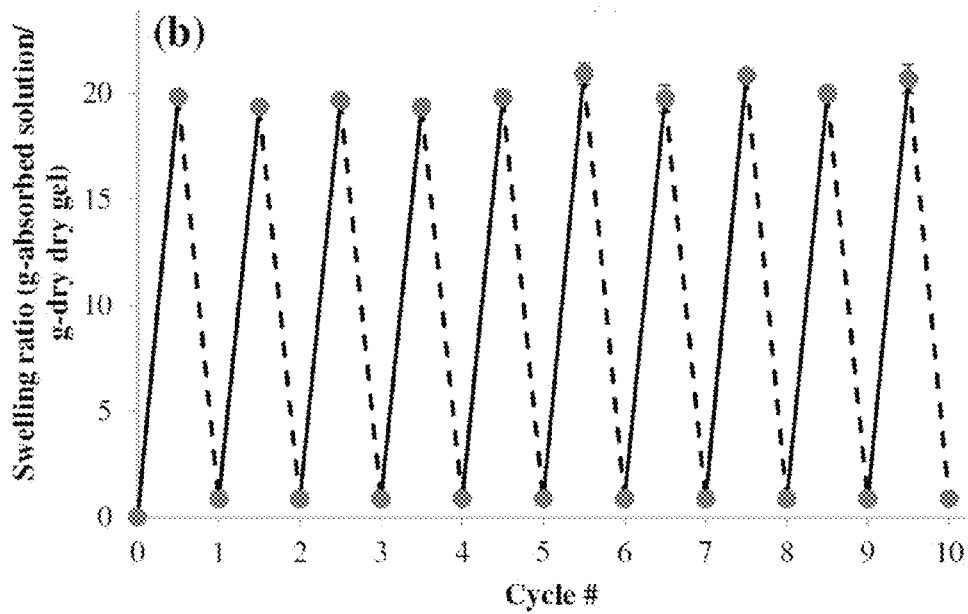

To assess consistency in gel performance over prolonged reuse, repeated swelling and deswelling of hydrogel samples were performed over multiple cycles. Hydrogels were swelled in microalgae growth media for 2h at 20° C., following which hydrogels were recovered and deswollen in an oven (37° C.) for 2h. The recovered gels were then reused to absorb fresh media and then deswelled again; this cyclic process was repeated 10 times. Swollen and deswollen gel weights were recorded during each cycle and were used to calculate swelling ratios. From FIG. 3B, the swelling ratios remained close to 20 g-absorbed solution/g-dry gel for each of the swelling cycle, demonstrating that reuse of hydrogels did not influence their absorption performance. These results indicate that hydrogels can be used for prolonged periods without replacement by new gel material.

Example 3

Stage-Wise Concentration of Microalgae Cultures Using PNIPAAm Hydrogels

The feasibility of using PNIPAAm hydrogels for harvesting microalgae cultures was evaluated by implementing a stagewise dewatering approach. In each stage, the added hydrogels absorbed a fraction of the growth media to cause a partial increase in culture concentrations. In order to keep the absorption rate high, the gels were allowed to swell only partially (and rapidly absorb the aqueous growth media) for approximately 2h. The mass of dehydrated hydrogels (absorbent) added to each stage was such that the volume of swollen gel (at the end of the 2h incubation) was equal to or less than the volume of free liquid remaining at the end of the stage operation. Adequate availability of free liquid at the end of the stage incubation period was important to keep all gels submerged for the entire duration of the incubation such that the absorption capability of all gels was utilized. In addition, the free liquid remaining at the conclusion of the stage operation permitted a quick and easy flow of algae-rich slurries through the mesh used during recovery of swollen gels and also helped to "wash down" the cells that might be physically adhered to gel surfaces. The mass of dehydrated hydrogel to add to each stage was assessed from the volume of culture fed to a stage, the expected swelling ratio of 20 g-absorbed media/g-dry-gel during the 2h stage-residence time, and the constraint of retaining at least half of the feed liquid unabsorbed in each stage.

Biomass concentrations in the aqueous streams were determined by measuring total suspended solids (TSS). For TSS estimates, culture samples were filtered through a pre-weighed glass fiber filter. Subsequently, the filter paper containing the algae cake was washed with pure water to dissolve inorganic precipitates, if any. Thereafter, the filter paper was carefully removed and dried in an oven at 50° C. until a constant weight was obtained. Dry weight of algae biomass collected on the filter paper was calculated as the difference in weight of the filter paper before and after filtration. The concentration was calculated by dividing the measured algae mass by the filtered culture volume.

During each stage, cultures at room temperature were placed in a beaker and exposed to shrunken hydrogels that had been previously deswelled at 40° C. A stir bar was used for keeping the suspension well mixed. At the end of the incubation period, the suspension was passed through a nylon mesh to separate the swollen gel pieces from the concentrated culture. The swollen gels collected on the mesh were deswelled in an oven to recover the absorbed growth medium. During deswelling, the oven temperature was maintained at 37-38° C. to prevent microalgal cells from losing viability. The volume of concentrated culture collected was measured with a measuring cylinder. A part of the concentrated culture was set aside for TSS measurements and the remaining volume was transferred to the next dewatering stage.

Figure 4:
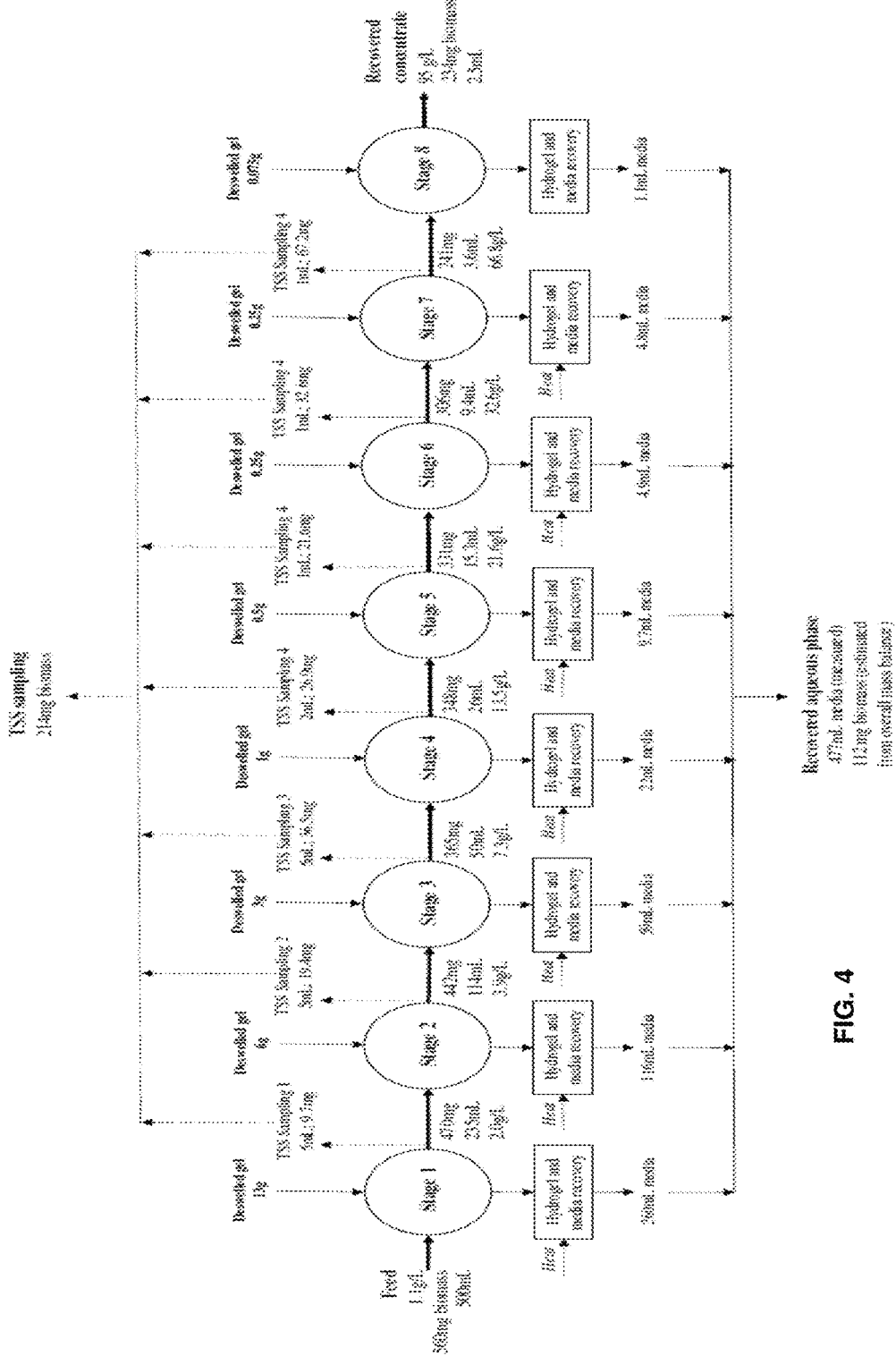
FIG. 4: First experimental run of a stage-wise concentration of microalgae cultures using PNIPAAm hydrogels.
Figure 5:
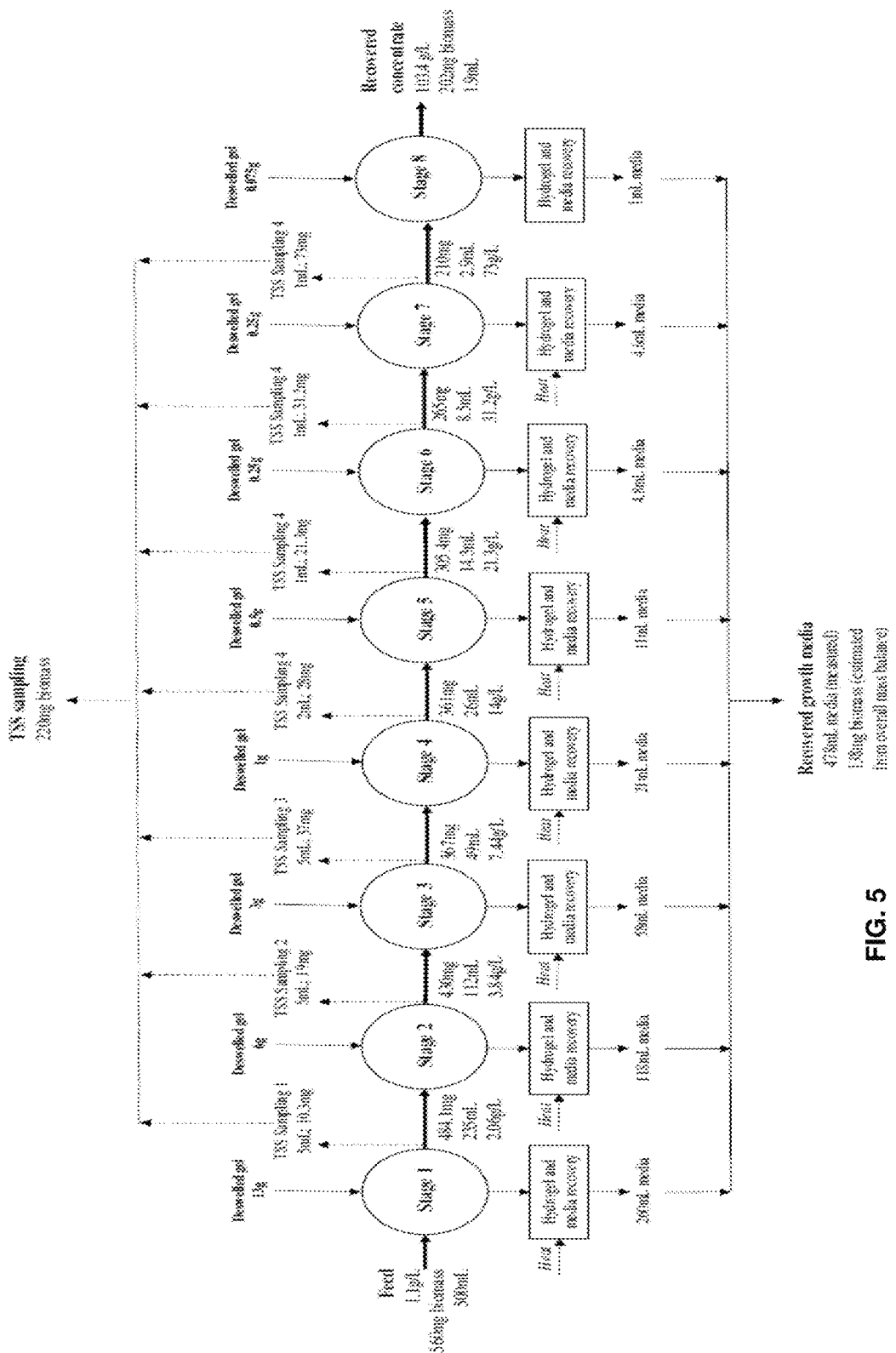
FIG. 5: Second experimental run of a stage-wise concentration of microalgae cultures using PNIPAAm hydrogels.
Figure 6:
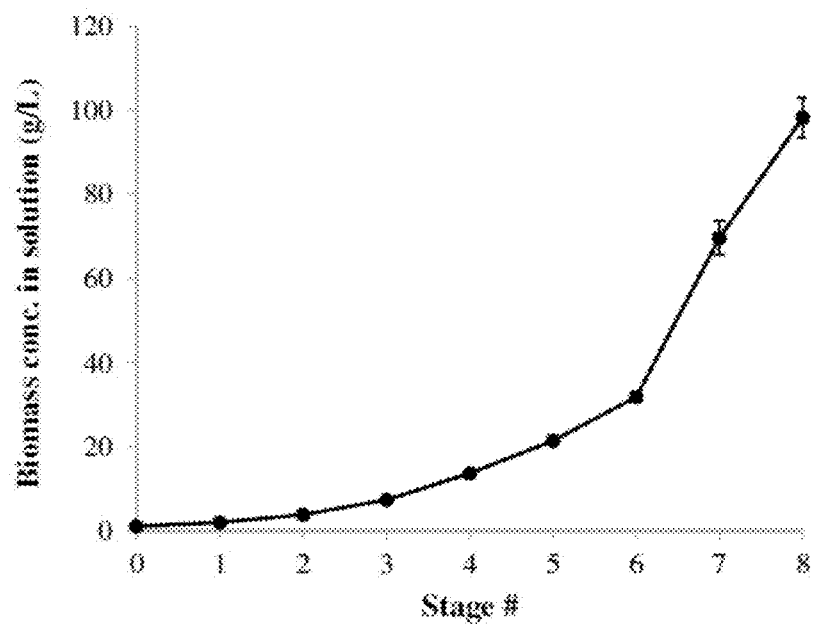
FIG. 6: Graph showing slurry concentrations at each stage of the stagewise concentration of microalgae cultures. Values shown in the graph are averaged from two replicate runs. Error bars indicate one standard deviation from mean values.

The results of the two experimental runs performed for stagewise implementation of microalgae harvesting using PNIPAAm hydrogels are shown in FIGS. 4-5. These figures show a detailed material balance for each stage of the process. An approximately 2-fold increase in concentration was achieved after each stage. Starting from an initial culture volume of 500 mL, >99% of the aqueous media was removed from the dilute feed such that <2.5 mL of the feed volume remained at the end of the 8-stage process. 90% of the culture media was recovered in only 3 stages. The concentrated cultures were approximately 100 g/L. The stage-wise increase in concentrations obtained during the implementation of this process is shown in FIG. 6. These experiments demonstrate that concentrations of 100 g/L or more can be achieved starting from dilute microalgae cultures.

Example 4

Synthesis of Rapid-Response Temperature-Sensitive PNIPAAm-PVA Semi-IPN Hydrogels and Characterization of their Swelling/Deswelling Kinetics In the previous example, stagewise implementation of the hydrogel dewatering method with PNIPAAm hydrogels allowed an increase in concentration from approximately 1 g/L to 100 g/L over 8 stages with a 2h duration per stage. While high final concentrations were achieved, the process time remained lengthy due to (1) the long residence time per stage due to relatively slow swelling kinetics of the hydrogels, and (2) the large number of stages due to the low mass of absorbent hydrogels used in each stage. Without wishing to be bound by theory, it is believed that the slow swelling rates of PNIPAAm gels are due to the limited hydrophilicity of these polymer networks. To improve swelling kinetics, the more hydrophilic poly (N-isopropylacrylamide)-polyvinyl alcohol hydrogel (PNIPAAm-PVA) with a semi-interpenetrating network (semi-IPN) structure was synthesized. While the presence of PVA does not change the LCST and thermal responsive properties of the underlying PNIPAAm, the semi-IPN is expected to display faster swelling kinetics relative to PNIPAAm due to increased hydrophilicity from the presence of PVA interlaced in the hydrogel structure. In addition, the interpenetration of two polymer networks also increases the mechanical strength of the polymer networks and improves the longevity of hydrogels during prolonged reuse.

Several other methods for improving hydrogel response rates such as copolymerization of PNIPAAm with comonomers, preparing macroporous gel by a phase-separation technique, and introducing mobile grafted hydrophilic chains, are possible. However, hydrogels prepared by these other techniques were deemed less suitable for hydrogel-based algae harvesting due to their potential for higher transition temperatures (and higher energy requirements for deswelling), large pore sizes that may entrap microalgae cells, or less favorable mechanical properties. For example, a copolymerization technique may weaken or even eliminate the thermal sensitivity of the PNIPAAm-based hydrogels due to the introduction of the non-thermosensitive moiety into the backbone of the hydrogel polymer.

The synthesis procedures for the PNIPAAm-PVA semi-IPN hydrogels were similar to the synthesis of PNIPAAm described in Example 1, with minor modifications. Polyvinyl alcohol (PVA) was first dissolved in distilled water at 70° C. before use. Then, the monomer NIPA, crosslinker BIS, and prepared PVA solution were mixed and dissolved well in distilled water to prepare hydrogels with specific compositions (see Table 1 for detailed composition). Thereafter, pure $N_2$ was bubbled through the mixture solution for 10 min to remove dissolved $O_2$. APS and Meta-BIS, as the initiator and the accelerator, respectively, were added last to induce and expedite the crosslinking and polymerization reactions. As before, a sealed glass cylinder was used as the polymerization reactor.

TABLE 1

Chemical components for semi-IPN hydrogels synthesis

| Component | Semi-IPN10 (High CD*) | Semi-IPN10 | Semi-IPN20 |
|---|---|---|---|
| NIPA | 7.128 | 7.128 | 6.336 |
| PVA | 0.792 | 0.792 | 1.584 |
| BIS | 0.072 | 0.05 | 0.05 |
| APS | 0.005 | 0.005 | 0.005 |
| Meta-BIS | 0.005 | 0.005 | 0.005 |
| Total volume (mL) | 118 | 118 | 118 |

*Cross-linker density (CD)

Polymerization reactions were carried out at room temperature for 10 h. Subsequently, formed hydrogels were removed from the cylinder and washed in DI water for at least 3 d, with the wash water being changed frequently to remove the unreacted chemical residues. The bulk of hydrogel was cut into small pieces with dimensions of approximately 3 mm×3 mm×3 mm using an onion chopper (Chop Magic, Allstar Products Group, Hawthorne, N.Y.).

Uptake rates of aqueous media by hydrogels was quantified by gravimetrically monitoring swollen gel weights over time. Before starting the experiment, prepared hydrogel pieces were dehydrated in an oven at 40° C. 0.5 g of dry gel pieces were weighed at room temperature, placed on a sheet of nylon mesh (approximately 6 cm in diameter) with a known weight, and incubated in fresh growth medium (composition of the growth medium is described in Example 1). As the hydrogels swelled, the nylon mesh along with the enclosed hydrogels was periodically removed and weighed, as described for PNIPAAm in Example 2. Hydrogels were allowed to swell until nearly-constant gel weight was achieved. Thereafter, swollen hydrogel pieces were transferred into warm growth media or an oven maintained at 40° C. for deswelling above the LCST. During the deswelling process, gels were periodically weighed at short time intervals (5-10 min) until constant weight was achieved.

Figure 7:
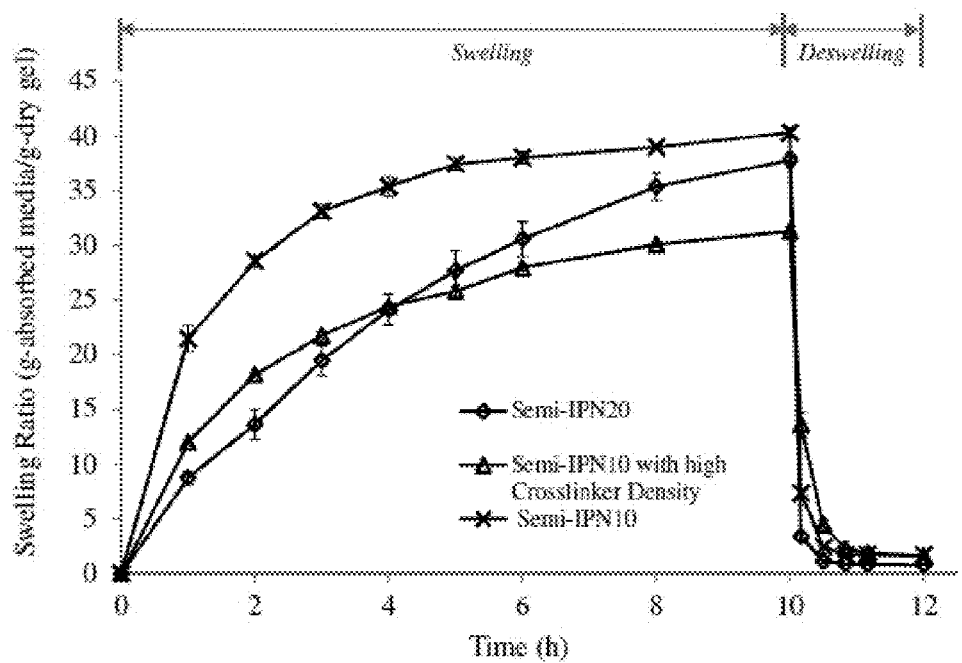
FIG. 7: Swelling and deswelling kinetics of PINIPAAm-PVA semi-IPN hydrogels in cell-free microalgae growth media. Error bars represent one standard deviation from mean values of triplicate experiments.

Changes in swelling ratios over time during swelling and deswelling in the growth medium are shown in FIG. 7. It can be seen that the swelling rate remained high only during the initial incubation period (0-4 h) and gradually decreased later. After 10 h, swelling rates were significantly diminished, indicating that the gels were close to their equilibrium swelling capacity. As with PNIPAAm, these results also indicate that a short residence time during the swelling stage is preferable in a harvesting process implemented with the semi-IPN gels. Additionally, compared to the swelling rates, the deswelling rates of all hydrogels were much higher. The deswelling periods are not likely to contribute as significantly to overall process times as the residence time during the swelling stages.

From FIG. 7, it can be seen that the PNIPAAm-PVA semi-IPN hydrogels with 10% PVA content (semi-IPN10) have an equilibrium swelling ratio of 40 g-media/g-gel after 10 h, and significantly faster overall water absorption rates than the other gels, including the PNIPAAm hydrogels described in Examples 1-3. The PVA chains, which were incorporated into the cross-linked PNIPAAm network, likely contributed to favorable swelling kinetics of semi-IPN10 gels. Without wishing to be bound by theory, it is believed the hydrophilic PVA chains are independent from the PNIPAAm backbone network and facilitated the increase in water uptake rates due to the favorable molecular interactions between polymer chains and water. However, too much PVA added in the network could also occlude the open pores (i.e., reduce the open channel area of pores), especially in de-swollen gels, and impede water uptake. The results show that the semi-IPN20 gels, which have a higher (20%) PVA content (based on PVA monomer added during polymerization), did not perform as well as the semi-IPN10 gels. Moreover, semi-IPN10 hydrogels with higher crosslinker density, synthesized in order to provide higher mechanical strength to the gels, also showed unfavorable gel swelling kinetics. Without wishing to be bound by theory, it is believed this was due to a reduction in effective pore size. Compared to the semi-IPN gels synthesized with higher crosslinker density, the structure of semi-IPN gels with the same PVA content and lower crosslinker density is more open with larger-sized pores since the polymer chains are not as tightly linked with each other.

PVA-containing semi-IPN gels also showed higher deswelling rates compared to PNIPAAm. Both the semi-IPN 10 and 20 gels were able to release more than 95% of absorbed media in 15 min (FIG. 7). In summary, the swelling and deswelling rates were greatly improved because of the introduced PVA chains, and semi-IPN10 gels had the best performance.

Example 5

PNIPAAm-PVA Semi-IPN Gel Performance During Re-Use

Figure 8:
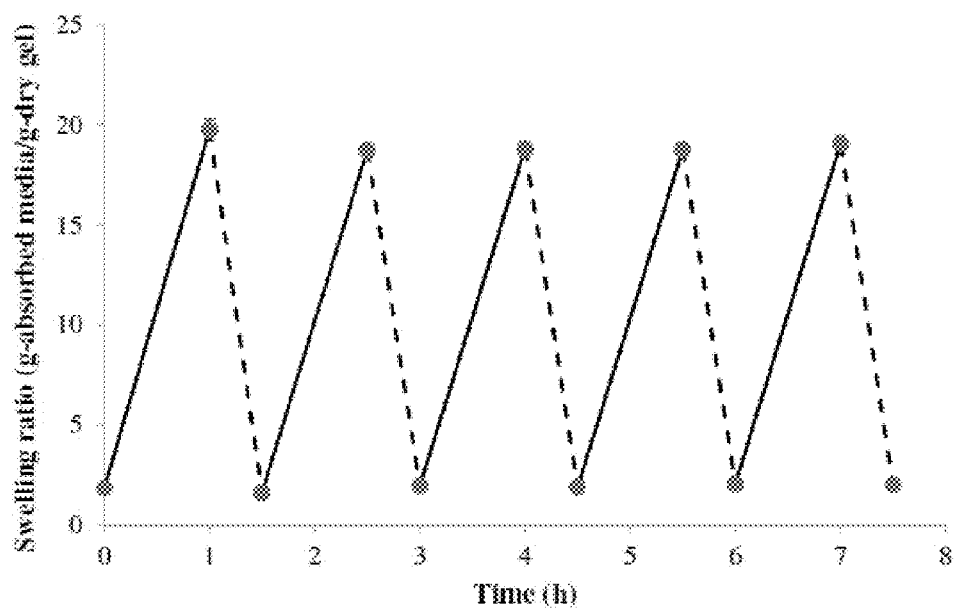
FIG. 8: Aqueous media uptake and release performance of PNIPAAm-PVA semi-IPN10 hydrogels when subjected to successive swelling-deswelling cycles. The solid and dashed lines represent the swelling (1h) and deswelling (0.5h) of each cycle, respectively.
Figure 9:
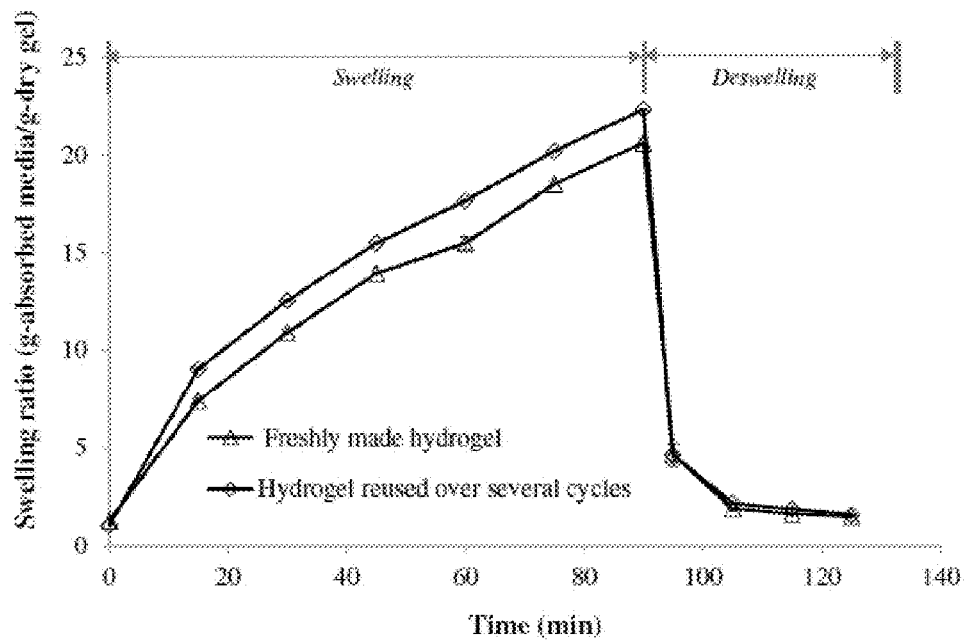
FIG. 9: Comparison of swelling kinetics between freshly-prepared semi-IPN10 hydrogels and gels that had undergone multiple (>30) swelling/deswelling cycles.

One conventional concern with semi-IPN hydrogels is that gels could lose performance over time due to loss of the intercalated PVA chains from the hydrogel network during the swelling and deswelling process. As such, the prolonged performance of the gels was evaluated. In these tests, semi-IPN10 hydrogels were repeatedly swelled (1h) and deswelled (0.5h), and no obvious change in kinetics could be observed over multiple successive uses of the gels (FIG. 8). The swelling kinetics were also assessed after the semi-IPN10 hydrogels had been used for several preliminary experiments to develop protocols for dewatering algae slurries (over 30 swelling and deswelling cycles). From FIG. 9, it can be seen that hydrogels that had been used repeatedly, in fact, exhibited slightly higher swelling and deswelling rates than freshly-prepared hydrogels. Thus, the swelling kinetics remain unaffected after repeated reuse of the gels. The consistent swelling/deswelling performance observed from these studies indicates that the semi-IPN10 hydrogels are suitable for prolonged use and do not need frequent replacements.

Example 6

Mechanical Properties of PNIPAAm and PNIPAAM-PVA Semi-IPN10 Hydrogels

In the hydrogel harvesting process, the mechanical properties of hydrogels play an important role in determining the durability, and thereby determine the cost of replacement of hydrogels. Hydrogels are soft materials that could be subjected to compression (due to hydrostatic forces) as well as shear (from the motion of aqueous media around the hydrogels) in large-scale harvesting equipment, depending on the design of the equipment. Therefore, the mechanical performance of the semi-IPN10 and PNIPAAm hydrogels when exposed to both kinds of stresses was tested. Further, the performance of fully- as well as partially-swollen gels was tested since repeated use of gels in a "fast kinetics region" (FIG. 3 and FIG. 7) would result in only partial swelling of the hydrogels.

The mechanical properties of hydrogels were characterized through compression tests and rheological measurements. To characterize the compressive resistance and deformation of hydrogels, a confined compression ramp stress protocol was employed. All compressive tests were conducted at room temperature using a bench-top mechanical testing device (Electroforce 3200, BOSE, Eden Prairie, Minn., USA) carrying a 100N load cell. Both fully-swollen and partially-swollen gels were tested with this method. Fully swollen hydrogels were cut into thin cylindrical pellets (thickness d: 3-4 mm; diameter Ø:17-18 mm) To prepare partially swollen gels, pre-dehydrated gels were swelled in water for 6h. Diameter and thickness of sample pellets were exactly measured and recorded with a digital caliper before starting the compressive test. To perform the tests, one flat end of each gel disk was placed on the sample plate, which had been covered with fine sand paper to prevent gels from slipping. Once the zero was set for the sample, a linear ramp compression displacement was applied to the sample at a strain rate of 0.1%/s until reaching 80% strain of the sample thickness. The stress was measured via the built-in force sensor of the load cell. A stress-strain profile ($\sigma$ vs. $\varepsilon$) was generated from the data collected.

For rheological measurements, a parallel-plate rotational rheometer (Rheometric Dynamic Analyzer Model 3, Rheometric Scientific, Piscataway, N.J., USA) was used for frequency-sweep tests. Tests were performed on thin cylindrical-shaped hydrogel samples (thickness d: approx. 3 mm; diameter 0: 17-18 mm) Both the fully- and partially-swollen gels were characterized. After gels were placed on the lower plate, the gap between the plates was set to either 3 mm (low vertical compression on gel surface) or 2 mm (with nearly 33% compression of gel). Thereafter, dynamic frequency-sweep tests at a constant 20% strain were recorded over the frequency range of 1.0-300.0 rad/s with a 1.0 rad/s increment.

Figure 10:
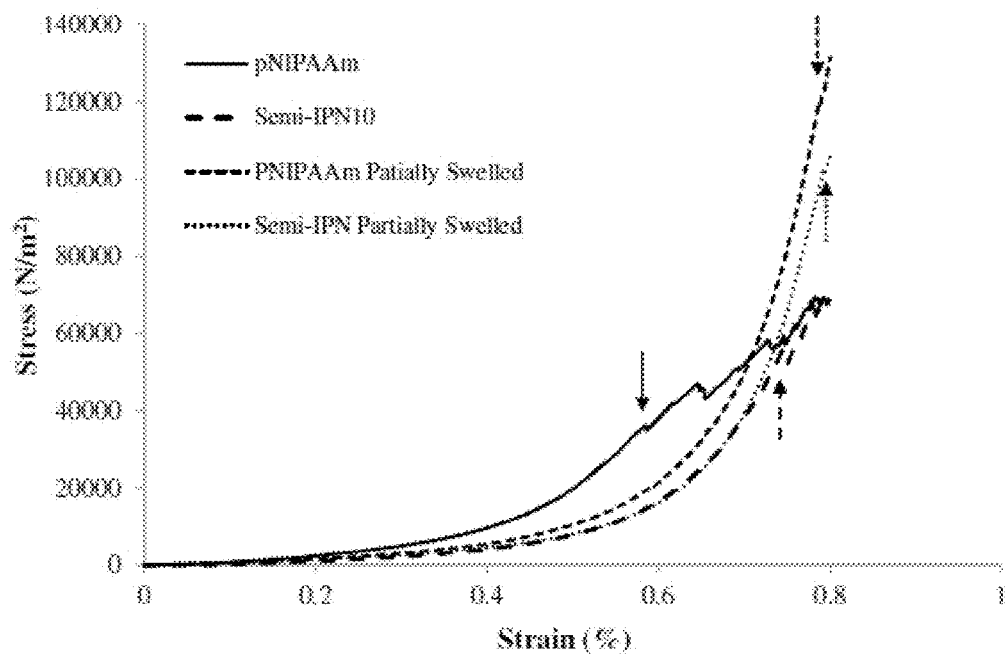
FIG. 10: Stress-strain curves for equilibrium-swollen- and partially-swollen gels. The arrows in the figure mark the onset of gel rupture as evidenced by a transition from smooth to jagged or irregular stress-strain curves.

The stress-strain plots from the compression tests are shown in FIG. 10. The arrows in the figure mark the onset of gel rupture as evidenced by a transition from smooth to jagged or irregular stress-strain curves. For equilibrium-swollen hydrogels, the rupture of the PNIPAAm gel sample occurred after 58% strain (corresponding to a stress of nearly 35.5 kN/m$^2$), while the semi-IPN10 gel sample was breached at a much higher strain of 75% (corresponding stress was nearly 54.5 kN/m²). These results indicate that the PNIPAAm-PVA semi-IPN10 gels show greater tolerance to compressive stress than the PNIPAAm gels. Moreover, rupture of the partially swollen gels (if any) occurred only at or beyond the maximum strains (80%) tested, indicating that partially swollen gels are significantly more resilient to breakage due to compressive stresses and therefore are more durable in large scale dewatering operations. Further, for both of the equilibrium-swollen- and partially-swollen-gels, the strain-stress curves of the PNIPAAm gel samples showed generally larger slopes than the semi-IPN10 gels, indicating that PNIPAAm gels are more rigid compared to the semi-IPN10 gels.

Figure 11A:
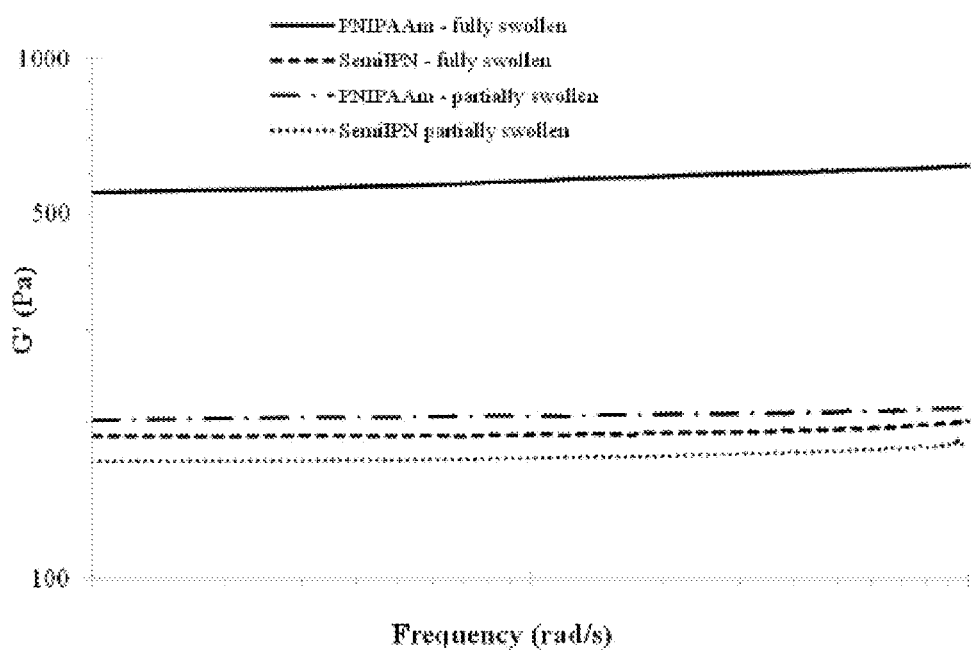
FIGS. 11A-11B: Frequency-sweep rheological characterization of equilibrium-swollen and partially-swollen PNIPAAm and semi-IPN10 gels.
Figure 11B:
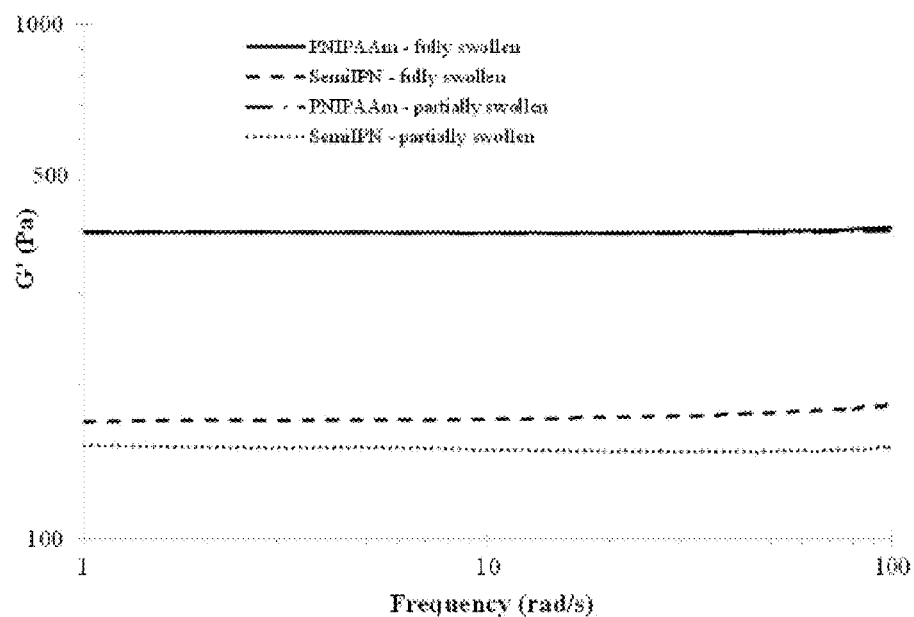

Rheological measurements were performed to assess hydrogel response to shear stresses alone or a combination of mechanical compression and shear. FIGS. 11A-11B show the results of frequency-sweep tests performed using a rotational rheometer. The elastic modulus G' was recorded as a function of frequency, increasing from 0 rad/s to 300 rads at a fixed amplitude $\gamma°=0.2$. In addition to rheological measurements on uncompressed gels (3 mm plate gap, FIG. 11A), G' values were also measured for gels that were compressed by setting the plate gap at 2 mm (approximately 33% compression of the gel, FIG. 11B). A characteristic feature of cross-linked hydrogels is that the values of G' remain largely unchanged over wide frequency ranges. The results are consistent with these previous observations. However, it was observed that the elastic modulus (G') of semi-IPN10 gel samples were always lower than G' values of PNIPAAm gels. Thus, the semi-IPN10 gels are more flexible (or less rigid) than PNIPAAm under shear and therefore are less susceptible to damage and attrition when exposed to fluid motion in the dewatering process. In addition, for hydrogel samples which were at partially swollen status, the elastic modulus G' was always lower than G' of equilibrium swollen gels, indicating that the partially swollen gels had greater elasticity than fully swollen gels and are more suitable in the dewatering process. Finally, as a result of the compression, the G' of both PNIPAAm gel and semi-IPN10 gel samples showed a decrease relative to uncompressed gels, likely due to loss in elasticity from the additional normal force (compare G' values between FIG. 11A and FIG. 11B). However, semi-IPN10 gels retained greater flexibility than PNIPAAm even under compression and the partially-swollen semi-IPN10 gels showed the lowest G' values (FIG. 11B).

In conclusion, these mechanical studies show that partially-swollen gels exhibit good resistance to compressive and shear damage and are therefore more suitable for the dewatering process than equilibrium swollen hydrogels.

Example 7

Stage-Wise Concentration of Microalgae Cultures Using PNIPAAm-PVA Semi-IPN10 Hydrogels As discussed in the previous sections, the semi-IPN10 gels showed highest initial swelling rates (FIG. 7), retained their performance over multiple cycles (FIGS. 8-9) and also had suitable mechanical properties for microalgae harvesting (FIGS. 10-11). Consequently, the feasibility of using the semi-IPN gels for concentrating microalgae cultures was tested by implementing a stagewise dewatering approach. As described in Example 3 (with PNIPAAm hydrogels), in each stage the added hydrogels absorbed a fraction of the growth media to cause a partial increase in culture concentrations. With a view to increase the rate of absorption per stage and reduce the overall process time, a residence time of 30 min per stage was targeted. In addition, it was desired to only absorb half of the feed volume per stage, such that gels would remain submerged during the entire incubation period and allow high retention of the cells in the concentrate (as also described in Example 3). These constraints allowed the mass of deswelled hydrogel to add per stage to be calculated. Due to the low residence time targeted, the mass of semi-IPN10 hydrogels calculated to be used relative to feed volume was higher than the mass of gel used in previous experiments with PNIPAAm (Example 3).

Figure 12:
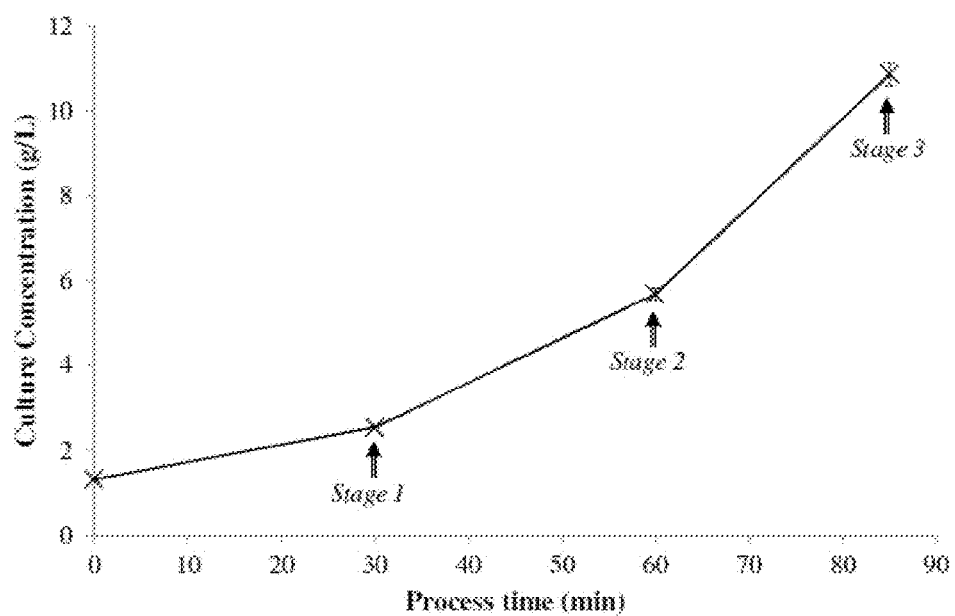
FIG. 12: Concentrations achieved during the stagewise dewatering using PNIPAAm-PVA semi-IPN10 hydrogels. The mass of deswelled hydrogels added to each stage for absorption of media were such that the ratio of feed volume to swollen hydrogel volume was between 2:1 and 1.7:1.

A three-stage dewatering process was implemented to demonstrate the feasibility of rapidly increasing culture concentrations. Two experimental runs were performed. Concentration changes of the microalgae culture with each process stage are shown in FIG. 12, where the horizontal axis shows the cumulative residence time through the process. These results show that more than 8-fold increases in concentrations were achieved through this stage-wise approach over a net residence time of 1.5h. Biomass concentrations of nearly 11 g/L were obtained over this period with removal of nearly 90% of the aqueous media. In the tests with PNIPAAm and low gel loadings, only a 2-fold increase in concentrations was obtained over a 2h period. Further, starting from a feed concentration of nearly 1 g/L, a process residence time of approximately 7h would be needed to obtain concentrations >10 g/L with PNIPAAm and low gel loadings. These results with semi-IPN hydrogels and high gel loadings are a significant improvement in hydrogel-based dewatering of microalgal cultures.

Stagewise mass balances for each of the duplicate 3-stage runs are shown in FIGS. 13-14, and are summarized in the stream tables accompanying these figures. From mass balances, 97% and 91% of the feed mass in Runs 1 and 2, respectively, could be accounted for through the process in the concentrate, sampling and dewatering streams. Visually, no algae cells were observed to be present within the gel and mass balance results also confirm no accumulation of biomass inside the gels. Without wishing to be bound by theory, it is believed that the small fraction of the feed mass (5-10%) recovered during the deswelling step was from cells adsorbed to gel surfaces.

Example 8

Viability of Microalgae Cells Recovered after Hydrogel Dewatering

Photosynthetic activity of the recovered cells (after hydrogel deswelling) was measured by Pulse Amplitude Modulated (PAM) fluorometry performed using a DUAL-PAM-100 Chlorophyll Fluorescence & P700 Photosynthesis Analyzer (Heinz Walz GmbH, Effeltrich, Germany). 5 mL sample was placed in the instrument vial. A stir bar was used to mix the sample. Then, the sample was kept in dark in the chamber for at least 5 min before starting the measurements of chlorophyll fluorescence parameters. Saturation pulse light intensity was set to 10000 µE.

In addition, the viability of microalgae cells recovered from hydrogel dewatering were assessed by direct re-cultivation. The concentrated cultures from dewatering were diluted in fresh medium to approximately 0.5 g/L before being re-cultivated. Dilute cells in the recovered medium were directly incubated without any further processing. As controls, microalgae cultures that hadn't been exposed to hydrogels were inoculated into fresh media and cultivated alongside the cultures recovered from the hydrogel dewatering process. Initial cell concentrations were kept similar between the cultures obtained from hydrogel dewatering (recovered medium and concentrate) and the controls to allow side-by-side comparison of growth performance. The recultivation experiments were performed in 400 mL photobioreactor (PBR101 Algae Photo Reactor, Phenometrics, Inc., Lansing, Mich., USA) in the presence of light (14 h/d) and with constant agitation. The pH was controlled at 8.5 by periodic sparging with a 5% $CO_2$-air mixture. Growth was monitored by measuring cell numbers using a flow cytometer (FLOWCAM, Fluid Imaging Technologies, Inc., Yarmouth, Me., USA). Samples from the ePBRs were first appropriately diluted to concentrations calculated to measure 10,000 cells/mL or lower. Camera focus was adjusted before taking measurements. 1 mL sample was analyzed by FlowCAM using the auto-image mode at an auto-image rate of 20 frames/s, 100× magnification (10× objective and 100-μm flow cell). The flow rate was set to 0.83 mL/min.

Results of PAM measurements are shown in FIG. 15. Cells in the recovered media showed good photosynthetic activity (as represented by the $F_v/F_m$) values close to 0.5, which indicates that the cells remained viable after incubation with the hydrogels and the subsequent deswelling operation. Thus, the hydrogels are not toxic to the algae. Without wishing to be bound by theory, it is believed that the small decrease in photosynthetic activity relative to fresh feed cultures was due to the slight thermal shock during the deswelling process which occurred at temperatures above ambient conditions (~38° C.). PAM measurements were made immediately after media and cells were recovered by hydrogel deswelling.

To more directly assess the viability of cells in the concentrate and in the media recovered after deswelling, direct cultivation experiments were performed. Fresh cultures that had never been exposed to hydrogels were used as positive controls. As shown in FIG. 16, cells in the deswelled media as well in the concentrate had growth similar to control cultures and positively confirmed that the hydrogel dewatering process did not result in any measurable loss in long-term cell viability. As a result, it is possible to recycle the recovered media and accompanying cells back into cultivation ponds or photobioreactors to reuse water and soluble nutrients. In cases where cell viability may be an important parameter in the value of the harvested biomass (e.g., nutraceutical products), hydrogel-based harvesting provides a superior product.

Example 9 pH Sensitive Hydrogels

In locations without sufficient low quality heat, temperature sensitive gels would incur costs of heating utilities. However, if waste $CO_2$ streams are available (e.g., from an ethanol plant or from an anaerobic digester), pH sensitive gels can be used for algae harvesting. These gels undergo swelling at alkaline pH (pH~8.5), which is the typical equilibrium pH of bicarbonate buffered algae growth media, and can undergo volume transition when pH is lowered below 6. For bicarbonate buffered solutions, such as algae growth media, pH shifts between 6 and 9 can be easily accomplished by using $CO_2$ as the acidifying agent ($CO_2$+ $H_2O \leftrightharpoons H_2CO_3 \leftrightharpoons HCO_3^- + H^+$). It was verified that bicarbonate-buffered growth medium, normally at pH 8.5, can be acidified to pH 6 at a $CO_2$ partial pressure of <2 atm. Removing the $CO_2$ pressure (and equilibrating with atmospheric $CO_2$) reinstates the solution back to its previous alkaline state. Since no temperature change (and thereby heating) is necessary to dewater algal slurries by pH-sensitive gels, this method is even more energy efficient than using thermo-sensitive gels. Double-responsive hydrogels that respond to changes in both temperature and pH can also be used at locations that have hot $CO_2$-containing streams such as flue gases from co-located power plants. These hydrogels, synthesized by co-polymerizing pNIPAAM with acrylic acid or methacrylic acid, have the additional advantage that the LCST also decreases when the pH is lowered such that more rapid de-swelling can be achieved even at room temperature if solutions are acidified to pH values below 6.

pH-sensitive poly(acrylic acid) (PAA) hydrogels were synthesized and tested for their ability to absorb and release algae growth media in response to pH changes. N,N-methylenebisacrylamide was used as the cross-linker for the hydrogel network. These components were added in an approximate 99:1 molar ratio. Deionized water was used as the solvent for the reaction. The initiator for the polymerization was ammonium persulfate and the accelerant used was sodium metabisulfate. The synthesis procedure was as follows: 7.134 g of acrylic acid and 0.154 g of N,N-methylenebisacrylamide were added to a glass vessel containing 90 mL of DI water. 0.012 g of ammonium persulfate and 0.05 g of sodium metabisulfate were added to a small test tube with 3.2 g of deionized water and dissolved completely, then poured directly into the reaction vessel. The solution was then sparged with $N_2$ for 10 min to remove oxygen, and allowed to polymerize for 24h under a $N_2$ atmosphere in the headspace. After polymerization, the gel was removed from the reaction vessel and placed in DI water to remove any unreacted chemicals. After two days of washing, the gel was cut into smaller pieces and placed in a medium supplemented with 0.25 g/L sodium carbonate to allow the hydrogels to fully swell. After allowing the gels to equilibrate in the buffer, they were cut into smaller pieces. Five samples of this gel were taken to be used in initial swelling and collapsing experiments. To determine equilibrium swelling and deswelling properties, the small gel pieces were first deswollen by lowering the medium pH with hydrochloric acid. The results of these experiments are shown in Table 2:

TABLE 2

PAA hydrogels deswelled in low pH solution

| Lot | Initial Mass (g) | Initial Deswelling pH | Deswelled Mass (g) | Swelling ratio 1 |
|---|---|---|---|---|
| B | 37.7321 | 1.92 | 3.36 | 10.22 |
| C | 38.4072 | 1.9 | 3.66 | 9.48 |
| D | 39.3557 | 1.9 | 3.85 | 9.23 |

Two of the gel samples were deswollen by sparging $CO_2$ through the solution. These results are shown in Table 3. Photographs of swollen gels and corresponding $CO_2$-facilitated deswollen gels are shown in FIG. 15.

TABLE 3

Deswelling PAA hydrogels by sparging with $CO_2$

| Gel sample | Swollen Weight (g) | Deswollen Weight (g) | Swelling Ratio |
|---|---|---|---|
| 1 | 1.99 | 0.19 | 9.36 |
| 2 | 1.38 | 0.11 | 11.49 |

Deswollen gels were again incubated in growth medium supplemented with sodium carbonate and allowed to swell. The data for these experiments is shown in Table 4.

TABLE 4

PAA hydrogel swelling in a medium supplemented with sodium carbonate

| Lot | Initial Mass (g) | Initial Swelling pH | Swollen Mass (g) | Swelling ratio 2 |
|---|---|---|---|---|
| B | 3.3631 | 11.22 | 32.23 | 8.58 |
| C | 3.6638 | 11.22 | 35.44 | 8.67 |
| D | 3.8489 | 11.22 | 37.56 | 8.76 |

Certain embodiments of the harvesting device and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A harvesting device comprising:
   a first end having a first opening in communication with a jacket, and a second end having a second opening in communication with an inner chamber, wherein the jacket at least partially surrounds the inner chamber;
   a first valve configured to control flow of a fluid into the jacket through the first opening;
   a second valve configured to control flow of a liquid into and out of the inner chamber through the second opening;
   a central tube extending through the inner chamber and in communication with the second opening;
   at least one bucket within the inner chamber having a horizontal mesh defining a bed, wherein the horizontal mesh holds segments of a hydrogel, and wherein the bucket is disposed at least partially adjacent to the central tube; and
   a plurality of one-way check valves configured to allow passage a fluid from the jacket into the inner chamber; wherein the central tube defines perforations configured to allow passage of a substance between the central tube and the bucket.

2. The harvesting device of claim 1, wherein the harvesting device includes a plurality of buckets.

3. The harvesting device of claim 1, wherein one or more of the jacket, inner chamber, or central tube is annular.

4. The harvesting device of claim 1, wherein the inner chamber is concentric with the central tube.

5. The harvesting device of claim 1, wherein the jacket is concentric with the central tube.

6. The harvesting device of claim 1, further including a pump connected to the second opening.

7. The harvesting device of claim 1, further including a gas source connected to the first opening.

8. The harvesting device of claim 1, further including a heat source configured to heat a fluid administered into the first opening.

9. The harvesting device of claim 1, wherein the hydrogel is a stimuli-sensitive hydrogel.

10. The harvesting device of claim 1, wherein the hydrogel is a semi-IPN hydrogel.

11. The harvesting device of claim 1, wherein the hydrogel comprises PNIPAAm.

12. The harvesting device of claim 1, wherein the bucket circumferentially surrounds the central tube.

13. A method of using the harvesting device of claim 1, the method comprising:
   filling the bed with a stimuli-sensitive hydrogel;
   introducing dilute algal cultures in a culture media onto the bed through the central tube;
   closing the second valve;
   allowing the hydrogel to absorb the culture media and swell, thereby creating a concentrated algal slurry in the inner chamber; and
   opening the second valve to remove a concentrated algal slurry from the harvesting device.

14. The method of claim 13, wherein the stimuli-sensitive hydrogel comprises a semi-IPN hydrogel.

15. The method of claim 13, further comprising the steps of:
   introducing a stimulus into the jacket through the first valve so as to force open the one-way check valves and introduce the stimulus into the inner chamber, wherein the stimulus causes the swollen hydrogel to deswell and release media; and
   removing the released media from the harvesting device through the second valve.

16. The method of claim 15, wherein the stimulus is heat or $CO_2$.

* * * * *